United States Patent
Gustafsson et al.

(10) Patent No.: US 10,467,470 B2
(45) Date of Patent: Nov. 5, 2019

(54) EYE-TRACKING ENABLED WEARABLE DEVICES

(71) Applicant: Tobii AB, Danderyd (SE)

(72) Inventors: Simon Gustafsson, Danderyd (SE); Anders Kingbäck, Danderyd (SE); Peter Blixt, Danderyd (SE); Richard Hainzl, Danderyd (SE)

(73) Assignee: Tobii AB, Danderyd (SE)

( * ) Notice: Subject to any disclaimer, the term of this patent is extended or adjusted under 35 U.S.C. 154(b) by 225 days.

(21) Appl. No.: 15/276,618

(22) Filed: Sep. 26, 2016

(65) Prior Publication Data

US 2017/0090564 A1    Mar. 30, 2017

Related U.S. Application Data

(60) Provisional application No. 62/329,719, filed on Apr. 29, 2016, provisional application No. 62/232,268, filed on Sep. 24, 2015.

(51) Int. Cl.
   G06K 9/00 (2006.01)
   G02B 27/00 (2006.01)
   (Continued)

(52) U.S. Cl.
   CPC ..... G06K 9/00604 (2013.01); G02B 27/0093 (2013.01); G02B 27/017 (2013.01);
   (Continued)

(58) Field of Classification Search
   CPC .. G06K 9/00604; G09G 5/34; G09G 2354/00; G09G 2340/0464; G02B 27/017; G02B 27/0179; G02B 27/0093; G02B 2027/0138; G02B 2027/014; G02B 2027/0187; G06F 3/04815; G06F 3/04845; G06F 3/012; G06F 3/0304; G06F 3/0485;
   (Continued)

(56) References Cited

U.S. PATENT DOCUMENTS 5,844,544 A   12/1998  Kahn et al.
6,351,273 B1  2/2002   Lemelson et al.
(Continued)

FOREIGN PATENT DOCUMENTS

EP   2670482       12/2013
JP   2010017407    1/2010
(Continued)

OTHER PUBLICATIONS

Hillaire et al., "Using an Eye-Tracking System to Improve Camera Motions and Depth of Field Blur Effects in Virtual Environments", 2008, Virtual Reality Conference, 4 pages.
(Continued)

*Primary Examiner* — Tat C Chio
(74) *Attorney, Agent, or Firm* — Samuel I. Yamron

(57) ABSTRACT

A system for determining a gaze direction of a user in a wearable device is disclosed. The system may include a display device, a primary lens, an illuminator, and a plurality of imaging device. The primary lens may be disposed in front of the display device. The illuminator may be configured to illuminate an eye of a user. The plurality of imaging devices may be disposed on or in the primary lens to detect light reflected by the eye of the user.

28 Claims, 15 Drawing Sheets

(51) Int. Cl.
*G02B 27/01* (2006.01)
*G06F 3/01* (2006.01)
*G06F 3/0481* (2013.01)
*G06F 3/0484* (2013.01)
*G06F 3/03* (2006.01)
*G06F 3/0485* (2013.01)
*G09G 5/34* (2006.01)
*A61B 3/113* (2006.01)

(52) U.S. Cl.
CPC ......... *G02B 27/0179* (2013.01); *G06F 3/012* (2013.01); *G06F 3/013* (2013.01); *G06F 3/0304* (2013.01); *G06F 3/0485* (2013.01); *G06F 3/04815* (2013.01); *G06F 3/04845* (2013.01); *G09G 5/34* (2013.01); *A61B 3/113* (2013.01); *G02B 2027/014* (2013.01); *G02B 2027/0138* (2013.01); *G02B 2027/0187* (2013.01); *G06F 2203/0381* (2013.01); *G09G 2340/0464* (2013.01); *G09G 2354/00* (2013.01)

(58) Field of Classification Search
CPC ... G06F 3/013; G06F 2203/0381; A61B 3/113
See application file for complete search history.

(56) References Cited

U.S. PATENT DOCUMENTS

| | | |
|---|---|---|
| 7,164,423 B1 | 1/2007 | Westen |
| 7,952,535 B2 | 5/2011 | Watanabe et al. |
| 8,228,315 B1 | 7/2012 | Starner et al. |
| 8,386,928 B1 | 2/2013 | Asch et al. |
| 8,393,239 B2 | 3/2013 | Horning et al. |
| 8,643,951 B1 | 2/2014 | Wheeler et al. |
| 8,793,620 B2 | 7/2014 | Stafford |
| 8,971,570 B1 | 3/2015 | Raffle et al. |
| 9,041,787 B2 | 5/2015 | Andersson et al. |
| 9,069,164 B2 | 6/2015 | Starner et al. |
| 9,201,578 B2 | 12/2015 | Scott et al. |
| 9,442,567 B2 | 9/2016 | Scott et al. |
| 9,507,418 B2 | 11/2016 | Yu et al. |
| 9,778,814 B2 | 10/2017 | Ambrus et al. |
| 9,804,671 B2 | 10/2017 | Taguchi et al. |
| 9,830,513 B2 | 11/2017 | Gustafsson et al. |
| 9,958,941 B2 | 5/2018 | Gustafsson et al. |
| 2001/0034218 A1 | 10/2001 | Hudecek et al. |
| 2002/0175897 A1 | 11/2002 | Pelosi |
| 2004/0108971 A1 | 6/2004 | Waldern et al. |
| 2004/0252277 A1 | 12/2004 | Thomas, Jr. et al. |
| 2005/0243054 A1 | 11/2005 | Beymer et al. |
| 2006/0069458 A1 | 3/2006 | Lee et al. |
| 2010/0309432 A1 | 12/2010 | Suzuki et al. |
| 2010/0328444 A1 | 12/2010 | Blixt et al. |
| 2011/0032365 A1 | 2/2011 | Yett |
| 2011/0175932 A1 | 7/2011 | Yu et al. |
| 2012/0272179 A1 | 10/2012 | Stafford |
| 2012/0274745 A1 | 11/2012 | Russell |
| 2013/0016070 A1 | 1/2013 | Starner et al. |
| 2013/0021373 A1 | 1/2013 | Vaught et al. |
| 2013/0050432 A1 | 2/2013 | Perez et al. |
| 2013/0050833 A1 | 2/2013 | Lewis et al. |
| 2013/0083003 A1* | 4/2013 | Perez ............ G06F 3/005 345/419 |
| 2013/0114850 A1 | 5/2013 | Publicover et al. |
| 2013/0169560 A1 | 7/2013 | Cederlund et al. |
| 2013/0300636 A1 | 11/2013 | Cunningham et al. |
| 2013/0328762 A1 | 12/2013 | McCulloch et al. |
| 2014/0184550 A1 | 7/2014 | Hennessey et al. |
| 2014/0300538 A1 | 10/2014 | Rijnders |
| 2014/0306891 A1 | 10/2014 | Latta et al. |
| 2014/0347623 A1* | 11/2014 | Inoue ............ G02B 27/0075 351/159.41 |
| 2015/0042558 A1* | 2/2015 | Massonneau ........ G06F 3/005 345/156 |
| 2015/0061996 A1 | 3/2015 | Gustafsson et al. |
| 2015/0062322 A1 | 3/2015 | Gustafsson et al. |
| 2015/0070654 A1 | 3/2015 | Brown, Jr. et al. |
| 2015/0103018 A1 | 4/2015 | Kamin-Lyndgaard et al. |
| 2015/0130714 A1 | 5/2015 | Onuki |
| 2015/0130740 A1 | 5/2015 | Cederlund et al. |
| 2015/0138073 A1 | 5/2015 | Hennelly |
| 2015/0138079 A1 | 5/2015 | Lannsjö |
| 2015/0138244 A1 | 5/2015 | George-Svahn et al. |
| 2015/0143293 A1 | 5/2015 | George-Svahn et al. |
| 2015/0149956 A1 | 5/2015 | Kempinski et al. |
| 2015/0193018 A1 | 7/2015 | Venable et al. |
| 2015/0205494 A1 | 7/2015 | Scott et al. |
| 2015/0219899 A1 | 8/2015 | Mack et al. |
| 2015/0261008 A1* | 9/2015 | Fujii ............ G02B 3/08 351/159.01 |
| 2015/0268799 A1 | 9/2015 | Starner et al. |
| 2015/0301592 A1* | 10/2015 | Miller ............ G06F 3/011 345/156 |
| 2015/0331240 A1 | 11/2015 | Poulos et al. |
| 2015/0346810 A1 | 12/2015 | Urbach |
| 2016/0048204 A1 | 2/2016 | Scott et al. |
| 2016/0081547 A1 | 3/2016 | Gramatikov et al. |
| 2016/0179336 A1* | 6/2016 | Ambrus ............ G02B 27/017 715/768 |
| 2016/0189430 A1 | 6/2016 | Kuehne |
| 2016/0191576 A1 | 6/2016 | Thompson et al. |
| 2016/0320625 A1 | 11/2016 | Von et al. |
| 2017/0075420 A1 | 3/2017 | Yu et al. |
| 2017/0090562 A1 | 3/2017 | Gustafsson et al. |
| 2017/0090563 A1 | 3/2017 | Gustafsson et al. |
| 2017/0090566 A1 | 3/2017 | George-Svahn et al. |
| 2017/0091549 A1 | 3/2017 | Gustafsson et al. |
| 2017/0177078 A1 | 6/2017 | Henderek et al. |
| 2017/0177079 A1 | 6/2017 | George-Svahn et al. |
| 2017/0316264 A1 | 11/2017 | Gustafsson et al. |

FOREIGN PATENT DOCUMENTS

| | | |
|---|---|---|
| WO | 2006111744 | 10/2006 |
| WO | 2017053966 | 3/2017 |
| WO | 2017053971 | 3/2017 |
| WO | 2017053972 | 3/2017 |
| WO | 2017053974 | 3/2017 |

OTHER PUBLICATIONS

Guestrin, E.D, et al., "General Theory of Remote Gaze Estimation Using the Pupil Center and Corneal Reflections", Biomedical Engineering, IEEE Transactions, vol. 53, No. 6, pp. 1124-1133, Jun. 2006, 9 pages.

Littlewort-Ford, et al., "Are your eyes smiling? Detecting Genuine Smiles with Support Vector Machines and Gabor Wavelets", Proceedings of the 8th Joint Symposium on Neural Computation, 2001, 9 pages.

Daugman J.G., "High Confidence Visual Recognition of persons by a Test of Statistical Independence", IEEE Transactions on Pattern Analysis and Machine Intelligence, vol. 15, No. 1 I, 1993, pp. 1148-1161, 14 pages.

International Patent Application No. PCT/US2016/053783 , "International Search Report and Written Opinion", dated Jan. 4, 2017, 12 pages.

Hamamatsu, Profile Sensor S9132 High speed frame rate sensor capable of acquiring two-dimensional projection data, Jan. 2014, pp. 1-10.

Karitans et al., Method for Compensation of Eye Movements in Adaptive Optics, Latvian Journal of Physics and Technical Sciences vol. 47, No. 3, Jan. 1, 2010, pp. 51-56.

International Application No. PCT/US2016/053777, Invitation to Pay Additional Fees and Partial Search Report dated Dec. 1, 2016, 8 pages.

International Application No. PCT/US2016/053782, International Search Report and Written Opinion, dated Dec. 12, 2016, 13 pages.

International Application No. PCT/US2016/053785, International Search Report and Written Opinion dated Dec. 20, 2016, 12 pages.

(56) References Cited

OTHER PUBLICATIONS

U.S. Appl. No. 15/276,448, Non-Final Office Action dated Nov. 22, 2016, 18 pages.
U.S. Appl. No. 15/276,563, Non-Final Office Action dated Nov. 25, 2016, 11 pages.
U.S. Appl. No. 15/276,592, Non Final Office Action dated Nov. 10, 2016, 29 pages.
U.S. Appl. No. 15/276,592, Final Office Action dated Feb. 28, 2017, 33 pages.
International Application No. PCT/US2016/053777, International Search Report and Written Opinion dated Jan. 24, 2017, 19 pages.

* cited by examiner

EYE-TRACKING ENABLED WEARABLE DEVICES

CROSS-REFERENCE TO RELATED APPLICATIONS

This application claims priority to Provisional U.S. Patent Application No. 62/329,719 filed Apr. 29, 2016, entitled "WEARABLE DEVICE COMPRISING A DISPLAY AND IMAGE SENSOR," as well as Provisional U.S. Patent Application No. 62/232,268 filed Sep. 24, 2015, entitled "WEARABLE DEVICE COMPRISING A DISPLAY AND IMAGE SENSOR," the entire disclosures of which are hereby incorporated by reference, for all purposes, as if fully set forth herein.

BRIEF DESCRIPTION OF THE INVENTION

In one embodiment, a system for determining a gaze direction of a user in a wearable device is provided. The system may include a display device, a primary lens, an illuminator, and a plurality of imaging devices. The primary lens may be disposed in front of the display device. The illuminator may be configured to illuminate an eye of a user. The plurality of imaging devices may be disposed on or in the primary lens to detect light reflected by the eye of the user.

In another embodiment, a system for determining a gaze direction of a user in a wearable device is provided. The system may include a display device, a primary lens, an illuminator, and a plurality of imaging devices. The primary lens may be disposed in front of the display device. The illuminator may be disposed on or in the primary lens configured to illuminate an eye of a user. The plurality of imaging devices may be disposed on or in the primary lens to detect light reflected by the eye of the user.

In another embodiment, A system for determining a gaze direction of a user in a wearable device is provided. The system may include a display device, a primary lens, a plurality of illuminators, and a plurality of imaging devices. The primary lens may be disposed in front of the display device. The plurality of illuminators may be disposed on or in the primary lens configured to illuminate an eye of a user. The plurality of imaging devices may be disposed on or in the primary lens to detect light reflected by the eye of the user.

BRIEF DESCRIPTION OF THE DRAWINGS

The present invention is described in conjunction with the appended figures.

Figure 1:
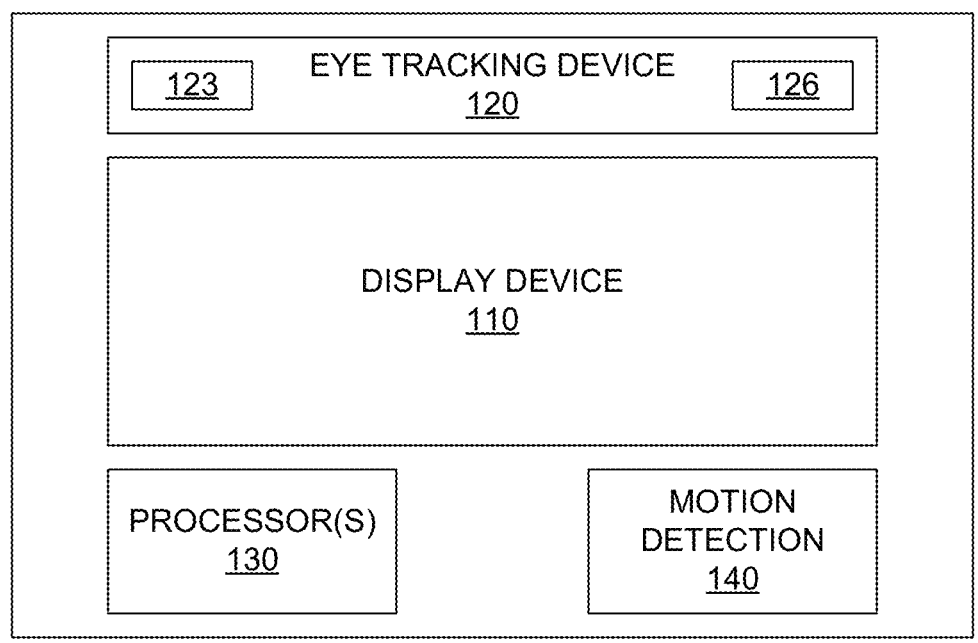
FIG. 1 shows an exemplary wearable device of the invention having a display device and an eye tracking device.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The present invention generally relates to a wearable device including a display and an image sensor, the wearable device uses information obtained through the image sensor to alter information on the display. In particular the present invention relates to systems and methods for utilizing information regarding an eye in altering information on a display.

Wearable devices containing displays are well known, typically they are utilized in Virtual Reality (VR) and Augmented Reality (AR) systems. In these systems the displays are used to provide a user with an experience that simulates either a different reality in the case of VR, or an enhanced reality in the case of AR.

In some cases the wearable device need not contain a display of any sort. For example a system described by U.S. Pat. No. 9,041,787 does not require a display. The entire contents of the aforementioned patent are hereby incorporated by reference, for all purposes, as if fully set forth herein.

In some embodiments, the use of eye tracking devices and the like can be incorporated with these wearable devices in order to improve their performance. For example, U.S. Patent Application Publication Number 2015/0062322 describes a wearable eye tracking device. The entire contents of the aforementioned patent publication are hereby incorporated by reference, for all purposes, as if fully set forth herein.

One implementation of eye tracking in a virtual reality device is described in Using an Eye-Tracking System to Improve Camera Motions and Depth-of-Field Blur Effects in Virtual Environments, Hillaire et al, 2008, Virtual Reality Conference, whereby eye tracking is used to determine a user's focus point in a virtual embodiment. The focus point is then used when rendering the virtual environment in order to improve the user's sensation when navigating the virtual environment. The entire contents of the aforementioned publication are hereby incorporated by reference, for all purposes, as if fully set forth herein.

Embodiments of the present invention seeks to provide improved solutions for eye tracking in wearable devices, and improved uses of eye tracking information in VR, AR, or other environments. These improvements may relate to hardware solutions for use in wearable devices, as well as software solutions for use with the same or similar devices.

Thus, an object of at least some embodiments of the present invention is to provide improved wearable eye tracking systems. This and other objects of embodiments of the present invention will be made apparent from the specification and claims together with appended drawings.

Various embodiments and aspects of the present invention will be arranged using headings herein, so as to facilitate more easy understanding of the present invention.

According to a first aspect of the present invention, there is provided a wearable device including at least a display and an eye tracking apparatus. Information from the eye tracking apparatus may be used by an associated computing device (for example, computer, tablet, mobile device, or other processor enabled device) to influence or alter items displayed on the display.

In some embodiments, the eye tracking apparatus includes at least one image sensor and at least one illumination source. In some embodiments the eye tracking apparatus may include two image sensors and two illumination sources. Any number of image sensors and illuminations sources are possible depending on the embodiment, and there may or may not be an equivalent number of image sensors and illumination sources. The illumination sources project illumination onto the eye(s) of a wearer of the wearable device, and the image sensor captures one or more images of the wearer's eye(s). Based on the location of reflection of illumination on the eye, a direction of the user's gaze may be determined. By way of example, a suitable system for determining the gaze direction of a user with a wearable eye tracking apparatus is described in U.S. Patent Application Publication Number 2015/0061996. The entire contents of the aforementioned publication are hereby incorporated by reference, for all purposes, as if fully set forth herein.

Connected directly or wirelessly to the eye tracking apparatus and display may be a computing unit or other associated processing device. The computing unit, or other processing device, performs calculations based on information from the eye tracking apparatus and controls information or other content displayed on the display, potentially after taking the calculations into account to modify the information or other content displayed on the display.

FIG. 1 shows a block diagram of a typical VR headset 100 with gaze tracking of various embodiments of the invention. Different embodiments of the invention may have fewer or greater number of components, and may be located/configured variably, as discussed herein. Headset 100 may include a display device 110, an eye tracking device 120 which includes illuminator(s) 123 and image/light sensor(s) 126. Illuminators 123 and image/light sensors 126 may include dedicated lenses. Processor 130 may provide computational/operational control for the components. In some embodiments, headset 100 may also include a motion/movement detection subsystem 140 do detect movement of headset 100. A communication bus, not shown, may provide for wired and/or wireless communication with an associated computing device.

Profile Sensor

In some embodiments, a profile sensor may be used to determine the gaze direction of a user. In these embodiments, a wearable device may be provided which include at least one profile sensor directed towards at least one of a user's eyes. An example of a suitable profile sensor is that manufactured by Hammamatsu with model number S9132. A profile sensor operates by summarizing the values of all pixels in a row and/or a column into a single value, as will be understood by one of skill in the art.

In addition, at least one infrared light emitter may be provided and directed towards the at least one of the user's eyes. In this manner, a profile sensor may be used to determine the location of a reflection of the infrared light from the user's cornea, otherwise referred to as a "glint." Rudimentary gaze tracking may thus be performed by analyzing the location of the glint on the user's cornea, as would be readily understood by one of skill in the art. In a further improvement, two or more profile sensors may be used. This offers several advantages.

First, if more than one two-dimensional profile sensor are used, it may be possible to determine the cornea center of a user's eye in three-dimensions, after determining the corneal radius and glint positions in three dimensions, as opposed to two dimensions.

Secondly, arranging at least two profile sensors such that resulting glints do not overlap allows for more accurate glint detection. For example consider a case with two glints cause by illuminators A and B. If they are imaged by a one-dimensional profile sensor aligned in the same direction as the glints, the sensor would only register a single response caused by both glints, so it would be difficult or impossible to determine whether the glint is caused by illuminator A, illuminator B, or both. Aligning the illuminators and profile sensors in such a way so that glints do not overlap in any readout of any profile sensor is therefore advantageous.

Alternatively, illuminators may be modulated to ensure that only one illuminator is lit at any given time. A profile sensor in such an arrangement may be designed to operate at very fast sampling rate, enabling many samples, and capturing a glint from only one illuminator at each sample within a short time frame to ensure only minimal eye movement between samples.

Thirdly, multiple one-dimensional profile sensors may be used. In order for such a system to function accurately each sensor must be placed and rotated relative to each other. In this manner the single dimension for each sensor could be alternated between being in horizontal and vertical configuration, although the relative orientation difference need not be limited to 90 degrees. Furthermore it may be desirable in these arrangements to add a cylindrical shaped lens to each one dimension profile sensor.

Figure 2:
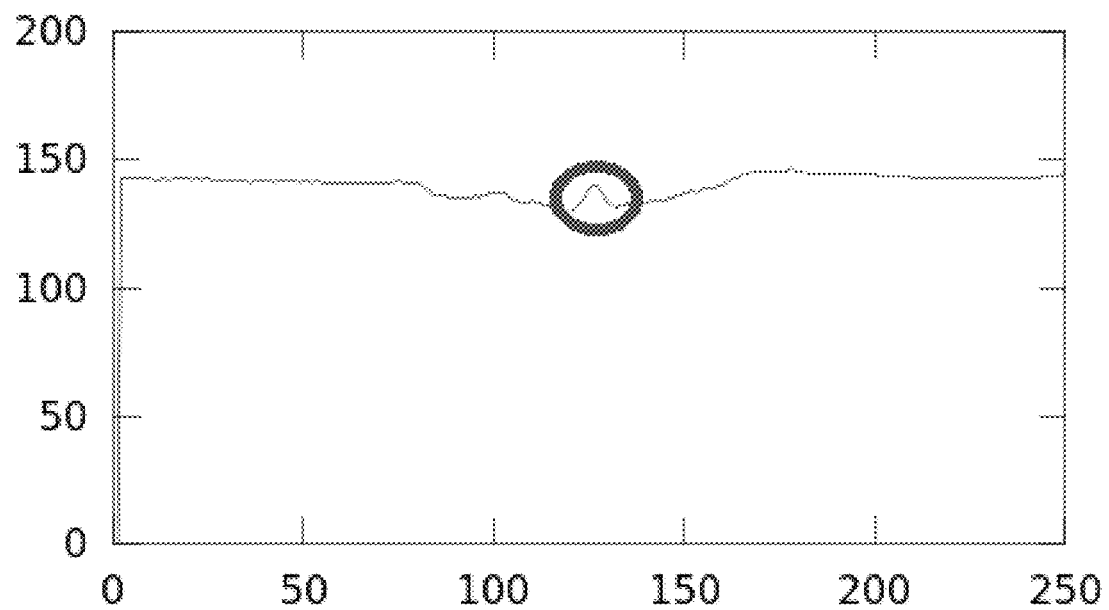
FIG. 2 shows an exemplary profile sensor output of various embodiments of the invention.

In some embodiments, the profile sensor may output the sum of all rows and/or the sum of all columns of the pixel matrix of the sensor to a processing device. A reflection of infrared light from the infrared illuminator on a user's cornea, known as a glint, may be found using a technique known as peak detection. Peak detection may be performed on both the sum of the rows and the sum of the columns. FIG. 2 illustrates this technique on an output of the sum of rows or columns, where the x-axis represents the pixels of the profile sensor, and the y-axis represents the magnitude, with an example of a peak highlighted.

In an optional improvement, in order to facilitate high speed eye tracking, where a previously calculated glint position is known—only a subset of pixels must be analyzed for a peak. For example, only 10-20 pixels close to the known previous glint position may be analyzed.

Once the glint position is known, gaze direction can be determined using, for example, a polynomial glint to gaze point model:

$$\text{gaze}_x = c_1 x + c_2 y + c_3 xy + c_4 x^2 + c_5 y^2 + c_6$$

$$\text{gaze}_y = c_7 x + c_8 y + c_9 xy + c_{10} x^2 + c_{11} y^2 + c_{12},$$

where $\text{gaze}_x$ and $\text{gaze}_y$ are the x and y positions of the gaze point, x and y are the x and y positions of the glint, and c1 . . . c12 are calibrated model parameters.

In some embodiments, more than one illuminator may be provided in combination with the profile sensor. These illuminators may be selectively enabled or modulated, and the processing device may determine which illuminator to enable based on metrics derived from captured image data. Alternatively, the illuminators may be lit in a predefined sequence ensuring that only one illuminator is lit at any given time.

In another embodiment, the wearable device further may contain at least one image sensor of the conventional area sensor type. This conventional sensor may also be directed to at least one of the user's eyes. The conventional sensor may capture images of a user's eye and the system may perform traditional Pupil Centre Corneal Reflection (PCCR) eye tracking. PCCR is a well-known and readily understood method of determining a user's gaze. Further information on this method can be found in multiple places, including Guestrin, E. D., Eizenman, E., "General theory of remote gaze estimation using the pupil center and corneal reflections," Biomedical Engineering, IEEE Transactions, vol. 53, no. 6, pp. 1124,1133, June 2006.

By combining a profile sensor, enabled to output the sum of all columns and/or the sum of all rows, with a conventional image sensor, the system may conduct glint tracking using the profile sensor, and PCCR tracking using the conventional sensor. Due to the additional information provided by the profile sensor, the conventional sensor then need only run at 0.5 to 10.0 Hz. Thus the system may achieve low power consumption, low latency, and a high frame (or sampling) rate.

A profile sensor tracking the glint will give sufficient gaze data as long as the sensor stays fixed relative to the face of the user, while the images from the conventional image sensor allow for slippage compensation whenever the sensor moves relative to the face. However, in general, eye movements are substantially faster than any potential slippage of a wearable device on the head of the user. So it is therefore of interest to find a way of only tracking the glint position at low power and low latency. This may allow for foveated rendering in VR headsets where a relatively low power eye tracking solution can allow for substantial savings in overall power consumption of the VR system, since graphics rendering power requirements can be significantly lowered.

For example, it may be possible to set the sensor in a mode where it cycles through two or more illuminators, having only one illuminator lit per sensor exposure. For example, the sensor may be set to run in a cycle where a first illuminator is lit during a first sensor exposure and then the sum of at least 10% of the pixel elements in at least 10% of the rows of the sensitive area and the sum of at least 10% of the pixel elements in at least 10% of the columns of the sensitive area are calculated (and a glint position is detected). Thereafter, a second illuminator is lit during a second sensor exposure and then the sum of at least 10% of the pixel elements in at least 10% of the rows of the sensitive area and the sum of at least 10% of the pixel elements in at least 10% of the columns of the sensitive area are calculated. Thereafter, the sensor captures a conventional image from at least a sub part of the sensitive area of the sensor while at least one of the illuminators is lit.

In an alternative implementation, the sensor may be set to run in a cycle where a first illuminator is lit during a first sensor exposure and then the sum of at least 10% of the pixel elements in at least 10% of the rows of the sensitive area are calculated. Secondly the first illuminator is lit during a second sensor exposure and the sum of at least 10% of the pixel elements in at least 10% of the columns of the sensitive area calculated. Thereafter, the sensor captures a conventional image from at least a sub part of the sensitive area of the sensor while at least one of the illuminators is lit.

An image sensor enabled to operate as a conventional image sensor, but also enabled to output profiles for the sum of pixel lines and/or the sum of pixel columns of the sensitive area, may include output pins for synchronizing the exposure of one or multiple illuminators with the sensor exposure.

An image sensor enabled to operate as a conventional image sensor, but also enabled to output profiles for the sum of pixel lines and/or the sum of pixel columns of the sensitive area, may also support daisy chaining, thus allowing two or more sensors to connect to a processing unit through the same data bus, for example, a MIPI CSI-2 interface.

An image sensor enabled to operate as a conventional image sensor, but also enabled to output profiles for the sum of pixel lines and/or the sum of pixel columns of the sensitive area, may further include means for detecting the distance to an object in its field of view. This may be done through "time-of-flight" analysis.

To compensate for ambient light profile data and/or conventional image data, an image sensor may from time to time be sampled without active illumination, i.e. without having any of the illuminators lit.

The image sensor may also be used to also identify the user for login, security, and/or other reasons through iris recognition.

An image sensor enabled to operate as a conventional image sensor, but also enabled to output profiles for the sum of pixel lines and/or the sum of pixel columns of the sensitive area may also be designed so that that each pixel can only be included in the sum of columns or the sum of lines when the sensor is operated in profile mode. For example, the pixel elements may be laid out in a checker pattern where only every other pixel may be summed into a row profile and the other pixels may be summed into a column profile.

Figure 3A:
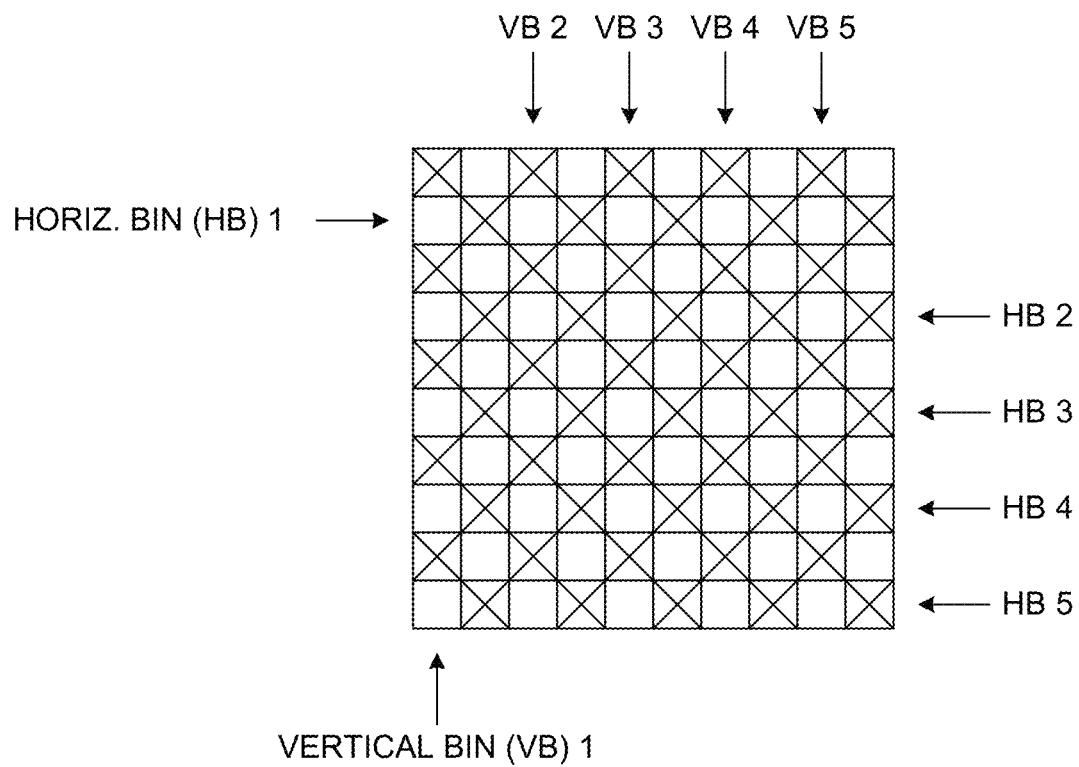
FIG. 3A shows horizontal and vertical pixel binning used in various embodiments of the invention.

An alternative implementation of the image sensor is to have the sensitive area split into a checker pattern where every other pixel is read out in rows and every other pixel is read out in columns, essentially having an AD converter next to each row, and an AD converter next to each column. This means that the conventional image for this sensor would be two images at half the sensor resolution, one read out vertically and one read out horizontally. This adds computational complexity for the traditional PCCR eye tracking. FIG. 3 demonstrates such a configuration in one example, as well as others discussed above, where an area image sensor emulating a profile sensor via its individual pixels, a 2D profile sensor, and/or two 1D profile sensors orientated orthogonally, can be employed in a manner whereby every other pixel of every other row (as marked with 'X') is used for horizontal glint/image data acquisition (horizontal bins 1-5), and every other pixel of every other column (also as marked with 'X') is used for vertical glint/image data acquisition (vertical bins 1-5).

The benefit would be that the sensor could be designed in such a way that it supports horizontal pixel binning for the image read out from each line and vertical pixel binning for the image read out from each column, thus facilitation low power glint detection. For example, the sensor could be designed to sum of the values from 8-16 pixel elements or even more into one value, meaning that it could operate as a profile sensor supporting sub-windowing functionality, which may facilitate suppression of irrelevant signals and lower noise.

A sensor enabled to operate as a profile sensor, with or without support for sub-windowing, may include HW logic for detecting the center of the glint, thereby further reducing power consumption and the amount of data required to send to an external processing unit. In the case that the sensor supports sub-windowing the sensor may change the sub-window position, after glint center detection, to ensure that a following profile image includes the glint.

An alternative implementation of an eye tracker supporting both traditional PCCR eye tracking, as well as glint tracking, to allow for low power eye tracking at latency and data rates supporting foveated rendering, is to have a regular sensor for imaging of the eye, but include HW logic for glint center detection when the sensor operates in a certain predefined sub-window mode. This may for instance only be possible with a sub-window of 24×24 pixels, 32×32 pixels, 48×24 pixels, or some other appropriate resolution.

In some embodiments, organic light emitting diode (OLED) displays may be employed. OLED displays are usually transparent, with a mirror placed behind them to ensure that all light is sent out forward, toward the viewer. For eye tracking purposes, a cold mirror may be located behind an OLED display essentially reflecting all visible light from the display towards the eye of the user but, letting through NIR light. In this manner, an eye tracking sensor detecting NIR light may be placed behind the display, looking through it, toward the viewer, thereby realizing an advantageous view angle towards the eye of the user.

In VR headsets it is also common to use Fresnel lenses to make the display appear at further distance from the user than it really is. The drawback of having a lens like this is that it distorts the image from the display and likewise it will distort the image of the eye as seen from an eye tracking sensor looking through the lens. It may therefore be preferable to compensate for this distortion in the eye tracking algorithms.

An additional effect of the Fresnel lens is that it may cause circular defects in the image of the eye, as seen from the eye tracking sensor. The pattern is similar to the distorting effect of waves on water when you throw in a small stone and try to look at something below the surface. It may therefore be preferable to calibrate an eye tracking sensor viewing an eye through a Fresnel lens to ensure that the images from the sensor are adjusted to compensate for the defects of the Fresnel lens, before machine vision algorithms try to detect different eye features or glints.

An image sensor enabled to operate as a conventional image sensor, but also enabled to output profiles for the sum of pixel lines and/or the sum of pixel columns of the sensitive area, may be designed to support sub-windowing. This is common in conventional image sensors, but by allowing sub-windowing when operated in profile mode, much of the potentially disrupting reflections or light sources in the field of view from the sensor may be removed before the pixel elements are summed up to a row profile and/or column profile, thus ensuring higher accuracy in the glint position determination, and allowing for re-centering of the sub-window for subsequent sample.

Figure 3B:
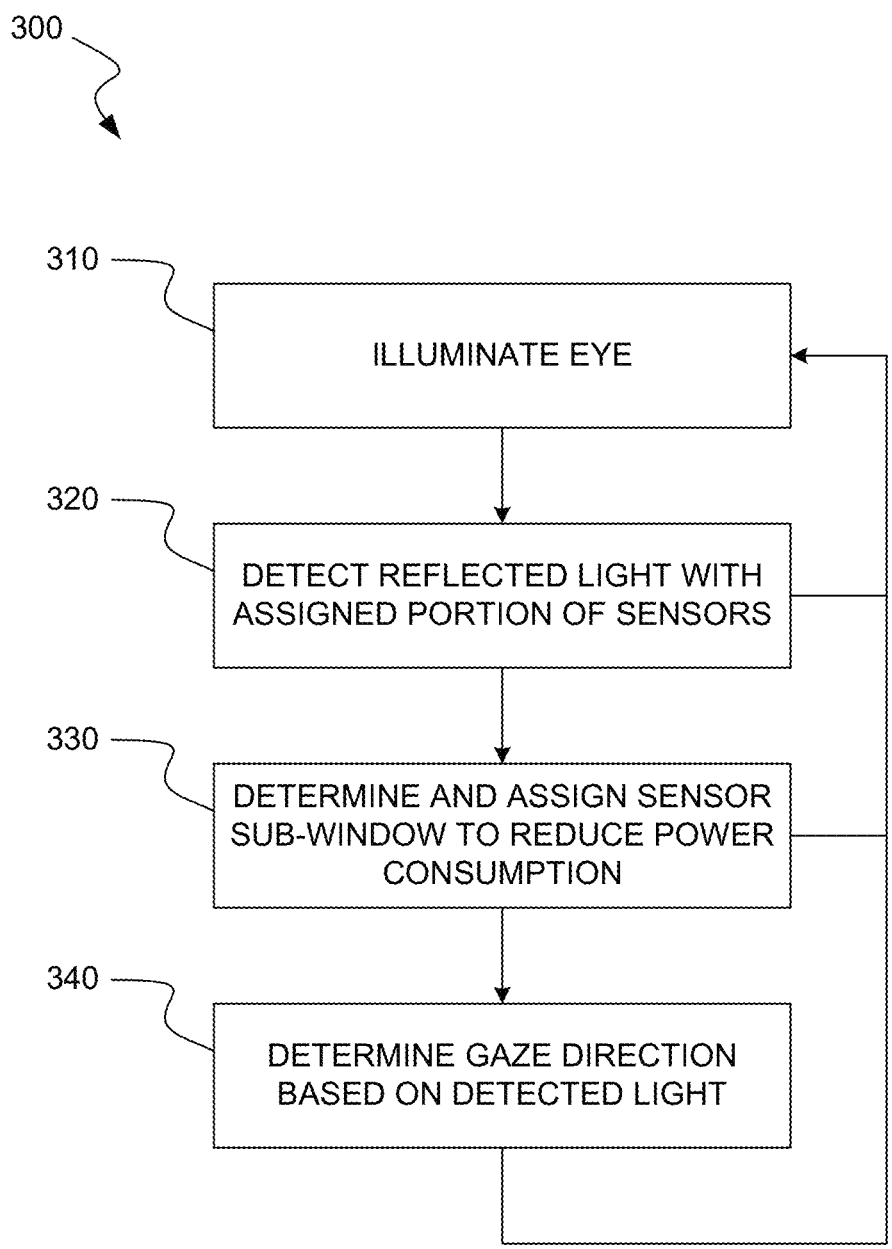
FIG. 3B shows one possible method embodiment of the invention for determining gaze direction.

FIG. 3B shows a block diagram of possible methods 300 described above for determining a gaze direction of a user. At block 310, one or more eyes are illuminated with one or more of the available illuminators. At block 320, one or more eyes are imaged via one or more of the available sensors (profile sensors and/or area image sensors). Blocks 310 and 320 may repeat as necessary. At block 330, as described above, the number of sensors and/or what portion thereof, may be limited to focus on a sub-window of likely pixels/resolution where imaging is likely necessary to determine gaze location. Blocks 310, 320, and 330 may repeat as necessary. At block 340, gaze direction may be determined, and blocks 310, 320, 330, and 340 may repeat as necessary to continually re-determine changing gaze direction and/or sub-windowing as necessary.

Hot Mirror

Figure 4:
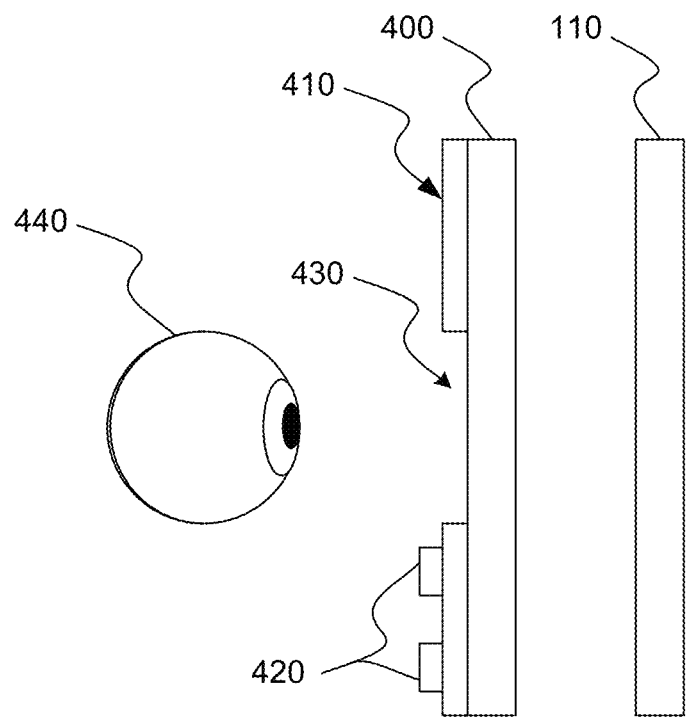
FIG. 4 shows one embodiment of the invention where a cold mirror is applied to a headset lens.

In one embodiment, as shown in FIG. 4, a lens 400 is provided in a wearable device such as a virtual reality headset. The lens 400 is positioned such that a wearer of the device may view a display 110 through the lens 400. Fixed atop the lens 400 is a hot mirror coating or film 410, and fixed atop the hot mirror film 410 are multiple illuminators 420. The film 410 has a cut-out portion 430 towards the center of the lens 400 to allow an eye tracking camera to view through the lens 400.

The hot mirror coating or film 410 may be applied directly onto the lens 400, or for ease of manufacturing, the hot mirror coating or film 410 may also be in the form of a separate piece which does not function as a lens. Further, and also for ease of manufacturing, a separate piece of glass or plastic may be placed atop the hot mirror, and the illuminators 420 may be affixed to this separate piece.

The illuminators 420 may emit infrared light outwardly towards the eye of a wearer 440, and then reflected by the eye of the wearer back towards the lens 400. The film 410 has the properties of a hot mirror, in other words the film 410 allows light in the visible spectrum to pass while preventing light in the infrared spectrum from passing. In this way, visible light emitted by a display 110 behind the lens 400 may pass to the wearer's eye, while most infrared light is prevented from passing.

An image sensor located behind the lens, and looking through the cut-out portion 430, captures images of the wearer's eye containing reflections of the infrared light emitted by the illuminators 420, a processing device connected to the image sensor then analyzes those images to determine a direction of the gaze of the user based on the reflections of the infrared light.

Although this embodiment has been described with reference to multiple infrared illuminators 420, it is possible for the invention to function adequately with only one illuminator.

Illuminators 420 may be applied to the film 410 in multiple ways, firstly simply through glue or alternatively a possible application is by printing electronics directly onto the film 410. The illuminators 420 will further have to have communication lines applied to the film 410 such that the illuminators may receive power so as to be turned on and off.

In one embodiment, the wearable device includes two lenses 400 with associated film 410 and illuminators 420. The film 410 may be applied to the lens through glue or some other semi-permanent substance. In a system with two lenses, light may reflect from the skin of a user into the lenses, whereby the lenses have a waveguide effect and channel the light away from the wearable device. The presence of the hot mirror 410 acts to lessen the emergence of this light.

In an alternative embodiment, the illuminators 420 may be placed on the side of the lens 400 (or additional pieces as previously described). Illumination from the illuminators 420 may then travel through the lens 400 to be emitted in front of the users eyes. This guiding of the light occurs in an area of the lens where the hot mirror 410 has been applied, so as to prevent illumination from being emitted towards the display 110.

In a further addition to the present invention, an angled hot mirror 410 may be added in front of the display 110, and the image sensor arranged to view the hot mirror. The lens 400 is then placed in front of a user's eye with illuminators 420 located adjacent thereto. The illuminators 420 illuminate the user's eye, and due to the lens 400 having a hot mirror film or coating, as has been previously described, stray illumination from the illuminators 420 is lessened. A cutout in the hot mirror film or coating allows the image sensor is able to capture images of the user's eye through the angled hot mirror.

Algorithms

In various embodiments, algorithms are used to determine, from an image containing an eye and reflections of infrared light from said eye, a gaze direction of the eye. A processing unit performs calculations based on algorithms using captured images to determine the gaze direction.

Algorithms used in wearable devices described herein are substantially similar to algorithms used in remote, existing eye tracking units. As such the fundamental approach to determining a gaze direction should be well understood by a person of skill in the art.

However, several improvements are discussed below.

Pupil Position

One step in determining a gaze direction in an eye tracking device is estimating the pupil's position and size. In some embodiments, the following method may be used to estimate pupil size and/or position.

In a captured image, the locations of reflections of the infrared light emitted by illuminators are analyzed to determine their location relative to a previous captured image. The displacements of the reflections, in combination with the pupil's position from a previous captured image, are next used to determine the pupil's position in the current image.

Fresnel Lens

When a Fresnel lens is present in a wearable device, an image captured by the eye tracking image sensor through the Fresnel lens typically contains concentric circles as are present in the Fresnel lens. These concentric circles can be mistakenly determined as pupil edges by the processing unit when attempting to determine gaze detection, therefore it is necessary to quickly and accurately remove these concentric circles.

In some embodiments, these concentric circles are removed from a captured image using erosion. Erosion is an image processing concept that would be well understood by a person of skill in the art. Using erosion, a small kernel, for example 3×3 or 5×5 pixels, is passed over the captured image pixel by pixel. For each pixel, the intensity value is replaced with the darkest pixel in the neighborhood of the pixel, where the neighborhood size is defined by the kernel. As the pupil in a captured image is dark, the light concentric circles in the captured image are therefore replaced by the dark pupil.

Masking Light

Another embodiment, allows for the use of hardware or software to perform mathematical operations along lines across a 2D image sensor to provide output similar to that of a profile sensor. The lines may typically be the rows and columns of that sensor, but won't necessarily be limited to these orientations. This would allow other operations than just the mean and/or sum of all pixel values on a line to be calculated, as well as making it possible to mask light contribution from parts of the image known not to contain any glints. Masking light contribution from parts of the image not containing any glints increases the signal to noise ratio, and hence aids in detection of the glint by allowing examination of the intensity profile of a profile response. In exemplary embodiments, the area to mask may be everything outside the cornea, and the most recent output from the eye tracking algorithms could be used to give an approximate area to mask.

Simulating a 2D profile sensor using a traditional image sensor reduces the computational load required for eye tracking and hence power consumption. However, framerate is limited to the framerate of the 2D imaging sensors.

It is possible to mask light contribution from parts of the image not containing any glints even when using a real profile sensor.

One method to mask light from parts of the image known not to contain any glints is through the use of one or several illuminators whose light can be spatially controlled (such as an infrared OLED array behind a lens, any arrangement with a DLP or LCOS projector, or a multitude of other solutions readily understood by one skilled in the art).

Yet another way to mask light from parts of the image known not to contain any glints is through the use of elements blocking parts of the light before entering the profile sensor. Those blocking elements could be LCD based, mechanical based, or based on a multitude of other solutions readily understood by one skilled in the art.

Simulating a Profile Sensor Using a Traditional Image Sensor

It is possible to utilize a traditional image sensor which includes a matrix of pixels to simulate a profile sensor, as discussed previously. To achieve this, hardware or software may perform mathematical operations (such as calculating the average intensity level along a line on the sensor or the sum of all intensity levels along a line on the sensor) to provide output similar to that of a profile sensor. Typically, this would equate to outputting rows or columns from the traditional sensor. However, it is possible to output any configuration of pixels, for example a diagonal line. By using this simulated system, it is possible to perform more operations than just the traditional mean and sum of all pixel values on a line, such as masking as previously described. Furthermore, it would be possible to mask detected light from areas of a captured image (pixels in the image sensor) known to not contain any glints. By performing this masking function, the signal to noise ratio may be increased. An example of an area to mask is the area outside of a user's cornea, as this area cannot contribute a glint.

The masking of light from areas of an image not contributing a glint may be performed using a traditional profile sensor. Further options for masking light include utilizing illuminators whose light may be spatially controlled, such as an infrared OLED array behind a lens, any arrangement with a DLP or LCOS projector, or any other solution readily understood by a person skilled in the art. Another option is to block light from non-contributing areas from reaching the sensor, this may be achieved by a mechanical solution, LCD solution, or any other solution understood by a person skilled in the art. A mechanical LCD solution may include placing a transparent LCD in front of a profile sensor.

Eye Tracker Synchronized with Display

For certain applications of eye tracking it is valuable to synchronize the eye tracking device with the display, particularly in a wearable device. In accordance with this aspect of embodiments of the present invention, a wearable device is provided with a display, at least one camera, and at least one illuminator. The camera(s) and illuminator(s) form an eye tracking device. Either the camera(s) and/or the illuminator(s) may be synchronized with the display. Synchronizing may be characterized as synchronizing the camera strobe rate with the v-sync of the display.

It is further desirable to synchronize the eye tracking device with a position device or devices. For example the eye tracking device may be synchronized with an inertial measurement unit or the like, or with a room position device which uses infrared or other non-visible light. Such a system has been proposed by Valve® under the name "Lighthouse". A person of skill in the art will readily understand how such synchronization may function.

Removable Eye Tracker

In accordance with another aspect of embodiments of the present invention, a removable eye tracker is provided whereby the eye tracker may be inserted into a wearable device. The eye tracker may then be integrated with another device such as a phone, tablet, watch, display or the like.

The eye tracker may include at least one camera and at least one illuminator, and its primary function may be to track a user's gaze relative to the device into which it is integrated, for example, a phone, tablet, or watch. As a secondary function, the device into which the eye tracker is sometimes integrated may be inserted into a wearable device. The device may then provide the wearable device with functionality such as a display, and the eye tracker may be used to determine the gaze direction of a wearer of the wearable device. The method of operation of the eye tracker may be any traditional method or any method described herein.

Smile Authentication

According to one aspect of the present invention an image sensor in a wearable device used for eye tracking may also be used to capture images of an area around a user's eyes. For example, these images may be analyzed to determine if a user is smiling, and whether that smile is genuine or fake. Characteristics of the areas around a user's eyes may be used to determine if a smile is fake or genuine. See, for example, Littlewort-Ford, Gwen, Marian Stewart Bartlett, and Javier R. Movellan, "Are your eyes smiling? Detecting Genuine Smiles with Support Vector Machines and Gabor Wavelets," Proceedings of the 8th Joint Symposium on Neural Computation, 2001. The entire disclosure of the aforementioned publication is hereby incorporated by reference, for all purposes, as if fully set forth herein.

According to embodiments of the present invention, an image sensor used for eye tracking captures at least a portion of the area around the eyes when capturing images of the eyes, these images may then be analysed using known smile or other detection algorithms to determine whether a user's smile or other facial feature is fake or genuine.

Calibration Based on Iris Identification

According to embodiments of the present invention, an image sensor used for eye tracking further captures information relating to a user's iris. This iris information can be used to determine the identity of the user for input into a system connected to the eye tracker.

For example, according to some embodiments of the present invention a wearable device is provided wherein at least one image sensor and at least one infrared illuminator is provided. The image sensor and illuminator faces toward an eye or eyes of a user wearing the device. Optionally, the device further contains a display such as in a Virtual Reality display in a wearable headset.

The image sensor captures images of the iris of the user and passes said images to a processing device, the processing device may be located on the wearable device or may be located remote from the processing device, in which case communication may be effected by wired or wireless means as would be understood by one of skill in the art.

Iris recognition is a known art and uses mathematical pattern-recognition techniques to uniquely identify a pattern on one iris, or both of a irises, of a user for identification or authentication of the user. In its most basic form, iris recognition includes the steps of (1) localization—calculating the inner and outer boundaries of the iris; (2) normalization—normalizing the captured data for consistency; (3) feature extraction—forming a feature vector of features extracted from captured images; and (3) matching—classifying the feature vector using thresholding techniques.

Many algorithms have been proposed which allow for iris recognition, see for example Daugman J. G., High Confidence Visual Recognition of Persons by a Test of Statistical Independence, IEEE Transactions on Pattern Analysis and Machine Intelligence, Volume: 15, No. 1 I, 1993, pp. 1148-1161. The entire disclosure of the aforementioned publication is hereby incorporated by reference, for all purposes, as if fully set forth herein.

Based on images of the user's iris, the processing unit connected (wired or wirelessly) with the wearable device may use the identification of the user to influence its function. For example when using an eye tracker, the processing unit may load a calibration profile which provides information specific to a user regarding an offset between their calculated gaze position and actual gaze position. By way of another example, the identification may be used to authenticate the user as authorized to operate the wearable device, or operate the processing unit connected thereto.

Eye Torsion Compensation

According to another aspect of embodiments of the present invention, it is possible to track eye torsion. By way of explanation, the human eye is attached to muscles in such a way that the eye, in addition to moving left/right and up/down, can also rotate such that the top of the iris may be rotated closer to the nose while the bottom of the iris rotates further away from the nose. The opposite rotation is also possible. This type of rotation is generally referred to as eye torsion.

When a human rotates their head slightly to their side, most humans automatically rotate their eyes slightly in the opposite direction, keeping their eyes close to level with the horizon. This effect is only in action during small rotations, since it's not possible to rotate the eye a large number of degrees in this way.

This phenomena introduces an additional source of errors in eye tracking systems for all persons whose fovea isn't perfectly centered along the optical axis of the eye.

The present invention may track eye torsion by watching the iris and/or other features on the eye ball and/or using orientation information from the eye tracker. This may provide the eye tracker with a better estimation of the position of the fovea, and hence would provide a better estimate of the gaze of the eye-tracked subject when their head is tilted.

Corneal Curvature

According to one embodiment of embodiments the present invention, the at least one image sensor captures images of a user's eye. The computing unit utilizes this information to determine the shape of the cornea of a user. Depending on the position and orientation of reflections from an infrared light source, the curvature of a cornea may be measured. In some people, their cornea has an abnormal curvature. This may be referred to as astigmatism.

By using information obtained from an image sensor and infrared light sources, the curvature of the cornea may be modeled and thus a user with an abnormally shaped cornea may be identified. By determining the shape of the cornea, corrective measures such as prescribing an appropriate lens may be performed.

Power Consumption and Processing Power Reduction

In some embodiments, to further reduce power consumption of a wearable device which may include a virtual reality display or other display system, an eye tracking device may only directly track a gaze position of a first eye of the user. The gaze position of the user's second eye may then be determined by a prediction which is based at least in part on the gaze position directly determined for the first eye.

This may be accomplished based on an assumption that the second eye is approximately on the same horizontal level of the first eye, as is biologically typical in human beings. In this manner, the power that would otherwise be used by an additional eye tracking device (including illuminators, image sensors, and/or processing power), may be saved. In some embodiments, the combined determined and predicted gaze positions of both eyes may then be used to determine a region for foveated rendering on a display of the wearable device, providing further power savings due to increase efficiency in video rendering.

In some embodiments, particular software such as gaming and/or other high-end graphical applications may request gaze data from the eye tracking device to inform the application of how to possibly interact with the user in the future, how much graphical information to provide a graphics processing unit, and/or other purpose. While in other embodiments all gaze direction information may be passed on to such applications, allowing individual applications to request such information, and only providing such information on request, may result in power and processing savings.

Virtual Reality Panning and Centering

In some embodiments, solutions are provided for easing the ability of a user to pan, and thereafter center, a virtual reality display or other display system in a user wearable device. Typically, because a virtual reality display is infinite in any direction (i.e., a user looking to the right in a virtual display will eventually turn 360 degrees to view the original scene), panning can become awkward for the user because they can only turn their head so much before it is uncomfortable for the user to continue turning their head.

In order to alleviate this issue, systems described herein may allow for a user to pan a view on the virtual reality display by turning their head and moving their gaze location toward a given direction in which panning will occur, but allow the displayed scene to be re-centered about a point when it is determined that, while the user's head has remains rotated, the gaze direction of the user has re-centered on the scene (i.e., their gaze location is no longer panning).

In some embodiments, re-centering of the gaze direction must occur for at least a predefined period of time to ensure that the user is indeed done panning their view. For example, the user's gaze must return to a relatively central region of the current view. The size, shape, and position of the region may, in some embodiments, be set by the user. In some embodiments, the region may be visible in different manners, potentially as set by the user (i.e., a lightly colored indication of the region may be overlaid onto other content on the display). In some embodiments, an indication (i.e., audible or visual cue) may be provided to the user to confirm that the virtual display view has been re-centered, and they may again move their head position to a straightforward, central, neutral position. This re-centering of the user's head may be allowed by the system without causing the display to be re-panned in the opposite direction of the original panning.

Similarly, if a user's gaze direction is also in the same direction as their head movement, or within a certain/predefined angular direction of each other, panning speed may start and/or be increased over situations where the user's head remains straightforward (i.e., where panning would stop and/or be decreased in speed), but their gaze direction indicates a pan is desired (i.e., by moving of the gaze direction to the peripheral view edges). Additionally, panning speed could be dependent on, and/or directly proportional to, the magnitude of the user's head movement. That meaning that large or sudden movements of the user's head could increase pan speed quickly, while small or slow movements of the user's head could increase pan speed slowly.

Figure 5:
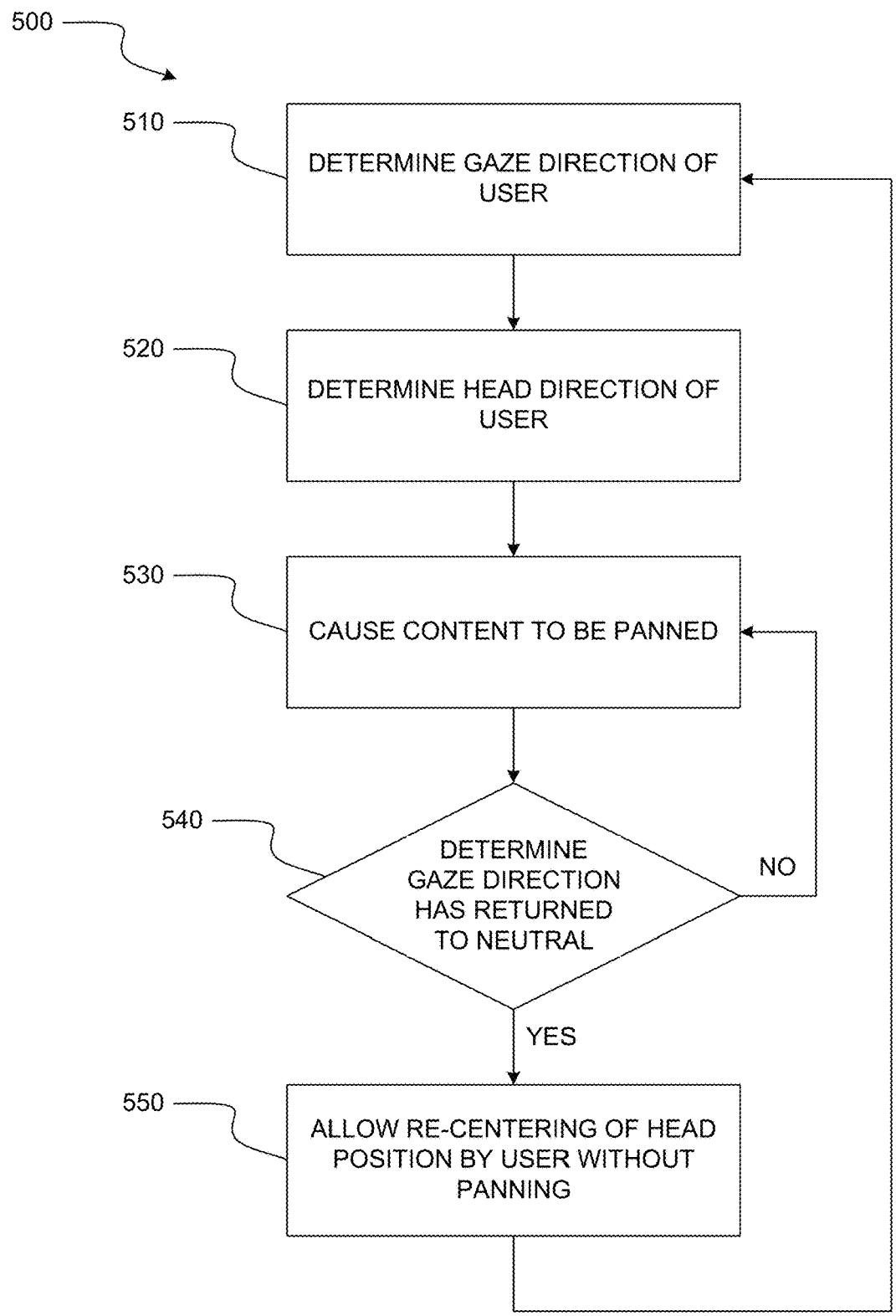
FIG. 5 shows one possible method embodiment of the invention for panning of a virtual reality display.

Thus, in one embodiment systems and methods for panning (and re-centering) content on a display of a wearable device may be provided. As shown in FIG. 5, the systems described herein may perform a method 500 which includes at block 510, determining, via an eye tracking device, a gaze direction of a user of a wearable device. The method may also include at block 520, determining, via a movement detection system, a head direction of the user of the wearable device. The movement detection system may include any internal/integrated or external/remote device to determine the head position of the user. The movement detection system may determine head position through any means now know, or later known, in the art.

The method may also include at block 530, based at least in part on the gaze direction and the head direction both being consistent with a particular direction, causing content displayed on a display of the wearable device to be panned in the particular direction. The method may also include, at block 540, determining during panning of the content, via the eye tracking device, that the gaze direction of the user has returned to a neutral position. The method may also include, based at least in part on the gaze direction of the user returning to the neutral position, causing content displayed on the display of the wearable device to stop panning.

Additionally, the head direction of the user exceeding a certain angular direction from a neutral/forward direction may also the panning direction/speed. Generally, speed of panning may be based on both the gaze and head direction.

An additional input may be provided by user to instruct the system to stop panning. Additionally, in some embodiments, the system may provide a visual and/or audible indication to the user that panning has stopped, and the user may move their head back to the forward/neutral direction without concern that panning in the reverse direction will occur (as shown at block 550).

Virtual Reality Mapping of Input Devices

In some embodiments, gaze detection may allow for mapping of input device actions onto the surface of a virtual object in a virtual reality display. For example, if a virtual sphere is located in the virtual space, the eye tracking device may determine that at some point the user's gaze direction is toward the sphere. Upon receipt of a secondary input, or the expiration of a predefined period of time, associated input devices may have their controls mapped to the virtual object.

The secondary input could include a contact input from a traditional input device such as a keyboard, touch pad (or other touch sensitive device), mouse, or trackball; or could also include a non-contact input such as a voice command or gaze input. More specifically, a contact input may have directional input on the touch sensitive surface controlling the mapping onto the virtual sphere to a user designated position; wherein the direction input means touch gesture; and the contact input may also pressure signal received from a pressure sensitive device associated with the touch sensitive surface; last but not least, the contact input can be combined with pressure touch and touch gesture. A proximity input may also be possible where the proximity touch input is received from touch sensitive device associated with a proximity sensor without physical contact with the touch sensitive surface.

Mapping control of an input device to the object may take many forms. For example, if a mouse is the input device being mapped, input from the mouse may determine a rotation of the object in virtual space, or may cause a visual indicator, such as a pointer, on the object to be moved about the virtual object. This may allow for complex actions to be executed by the user using the virtual object.

In another example, a virtual control panel having many virtual inputs such as switches and knobs may be present in the virtual reality display. Upon determining that the gaze direction of the user is directed to the virtual control panel, and that either a predefined period of time has passed or a secondary input has been received, controls of a keyboard or mouse may be mapped to the control panel. This may allow keys of the keyboard to be correspondingly mapped to the control panel, or mouse movement to cause a visual indicator or pointer (i.e., a visual representation of the user's hand) to be moved across the control panel to select or activate various virtual inputs thereon.

In some embodiments, a predefined portion of the virtual control panel (or other virtual object) may be the area in which the user's gaze direction must lie to activate control mapping (rather than the user's gaze direction being located anywhere on the control panel). In some embodiments, the predefined portion may be visually indicated and/or labeled in the virtual display.

Figure 6:
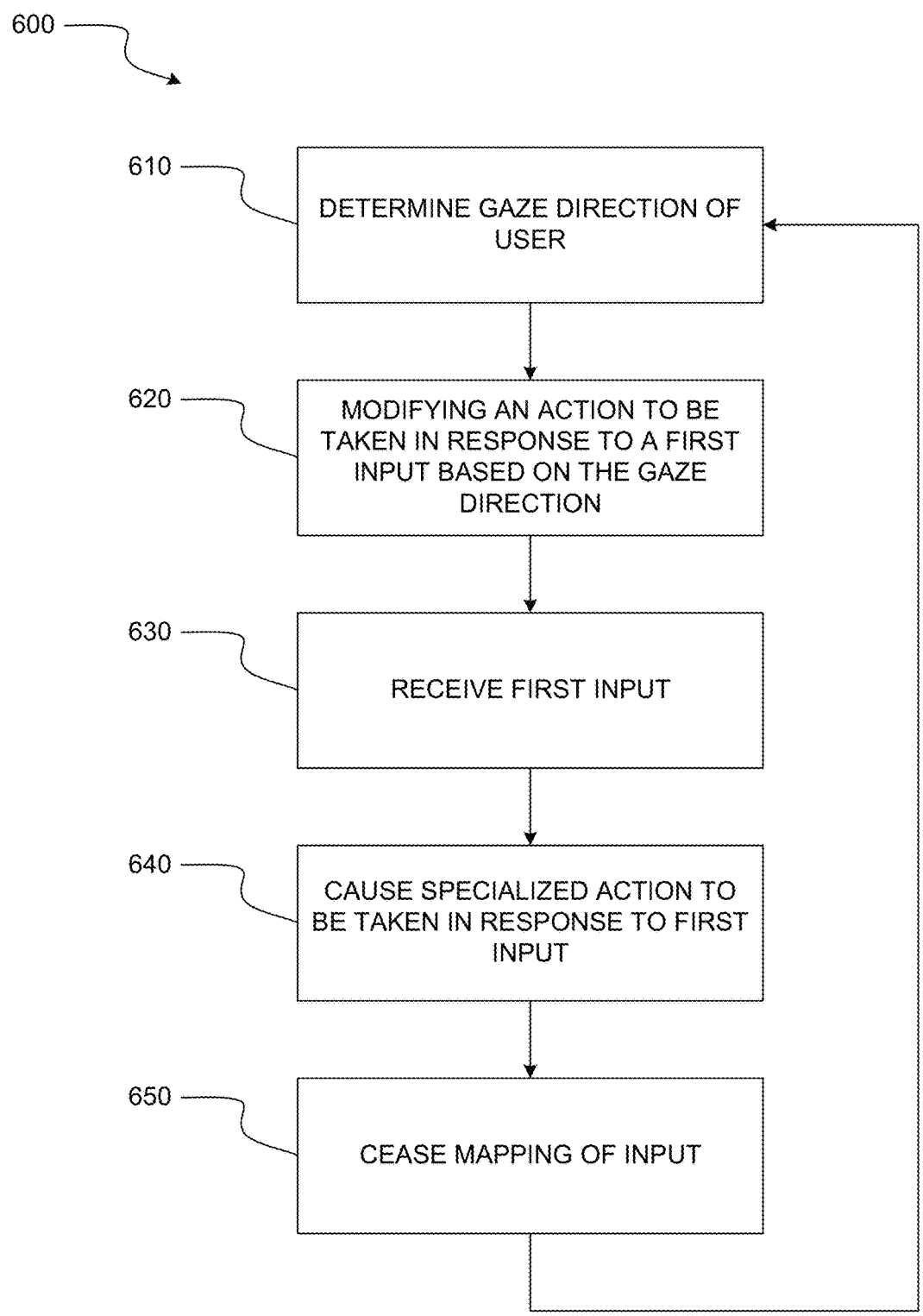
FIG. 6 shows one possible method embodiment of the invention for mapping input devices to virtual objects.

Thus, in some embodiments, systems which perform the methods discussed herein may be provided. In one example shown in FIG. 6, a method 600 for mapping an input device to a virtual object in virtual space displayed on a display device may include, at block 610, determining, via an eye tracking device, a gaze direction of a user.

The method may also include, at block 620, based at least in part on the gaze direction being directed to a virtual object in virtual space displayed on a display device, modifying an action to be taken by one or more processors in response to receiving a first input from an input device. This may also occur in response to the gaze direction being directed to the virtual object for at least a predefined period of time, or while a secondary input is received. The user may also be notified by visible/audible indication that the potential action has been modified.

Modification of the action may include modifying the action from a normal action to be taken in response to receipt of the first input to a specialized action in the virtual space associated with the virtual object. The specialized action in the virtual space associated with the virtual objection may be causing the first input to rotate the virtual object and/or cause the first input to move the virtual object. In these or other embodiments, the specialized action in the virtual space associated with the virtual object may be causing the first input to move a secondary object about the surface of the virtual object. The secondary object may move in a direction corresponding to a direction associated with the first input, and may be a pointer or other virtual location marker.

The method may also include, thereafter, in response to receiving the input from the input device, at block 630, causing the action to occur at block 640, wherein the action correlates the first input to an interaction with the virtual object.

In response to some input of a user, perhaps a tertiary or other input, after a certain amount of time has passed, or because their gaze has moved away from the virtual object in question, mapping of the input to the virtual object may cease, as shown at block 650.

Merely by way of example, input devices which could be mapped include, a touch sensitive device, a touch sensitive screen, a pressure sensitive device, a mouse, a trackball, a joystick, a handheld controller, a stylus, a keyboard, a speech input device, and/or any other input device discussed herein or known in the art.

In some embodiments, the apparent effect of an input device mapped to a virtual object as described herein may be magnified or de-magnified, as will be perceived by the user upon operation. Merely by way of example, in an embodiment where a user is rotating a virtual representation of a planet, a very small movement input of a mouse which is mapped to that virtual object may cause a large degree of spin of the virtual planet. Conversely, where a user is rotating a virtual representation of a molecule, a very large input of a mouse which is mapped to that virtual object may only cause a small degree of spin of the virtual molecule. The amount of magnification or de-magnification may depend on another input as set by the user, or may be pre-programmed into the particular application. The magnification or de-magnification may also be variable depending on various user and program set variables.

Saccade Predicted Areas of Interest in a Display

In some embodiments, saccades by a user's eye(s) may be detected, and used to estimate or determine where the user's gaze direction will lie upon completion of the saccade. Additionally, saccades for different individual users can be analyzed, and information related thereto stored, to predict future changes in gaze direction for a particular user upon occurrence of saccades thereby (i.e., saccades of different speeds for different users result in different angular changes of gaze direction).

Furthermore, known salient regions or objects of interest may also inform any prediction algorithm of the likelihood that a user's gaze direction will eventually lie thereon upon completion of a saccade in the direction of the region or object. The gaze direction patterns of a user, including the lengths of time a user's gaze direction lies on a given region or object, may also be analyzed to determine whether such regions or objects are particularly salient for when they are displayed in the future.

Consequently, the above information regarding user saccades and gaze direction changes, whether in the direction of known or unknown salient regions or objects, may be used to implement foveated rendering. For example, if a known salient region or object is to be displayed in the virtual display, and upon display of the region or object, the user's eye(s) saccade toward the region or object, the region or object may be rendered in greater quality prior to the user's gaze direction arriving thereon.

Even when the saliency of a region or object is unknown when displayed, or when no particularly salient region or object is being displayed, an angular change in gaze direction, and corresponding likely resulting viewing region, may be determined or estimated by detecting a saccade is occurring. The determined or estimated amount of angular change in gaze direction may be particular to the user based on previous recorded saccade data therefor, or may be default data applicable to all users, perhaps prior to recorded data for a particular user is available.

In some embodiments, if saccade information does not allow for precise determination of the user's likely resulting gaze direction, multiple known salient regions or objects which are located at the most likely gaze directions may be rendered in greater quality. In some embodiments, the increase in rendering quality for each region or object may be proportional to the likelihood that the user's gaze direction may eventually lie thereon. For example, if two regions are equally likely to be the resultant gaze area of a user's saccade, rendering quality for both regions may be increased similarly. However, if one region is the more likely resultant gaze area, then its rendering quality may be improved to a greater degree than the less likely resultant gaze area.

Figure 9:
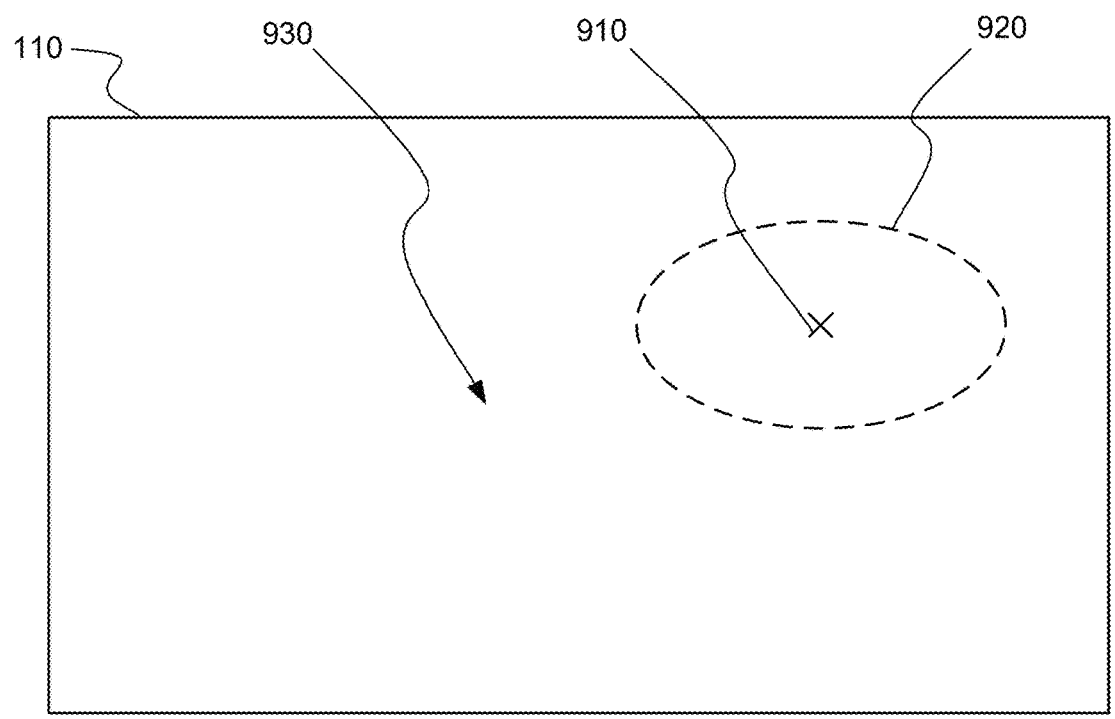
FIG. 9 is s a view of a display device of the invention in which image modification is occurring in response to a user's gaze point.

The way in which the image displayed on display device 110 may be modified by graphics processing device may vary depending on the embodiment, but regardless, the way in which the image is displayed may be intended to increase the image quality of portions of the image on which a user's gaze, or focused gaze, is directed, relative to those portions of the image to which the user's gaze, or focused gaze, is not directed. In this manner, the use of available resources of graphics processing device, and/or other system resources, are maximized to deliver image quality where it matters most on display device 110. To demonstrate, FIG. 9 illustrates a display device 110 showing a user's gaze point 910 and an area 920 around user's gaze point 910 in which embodiments of the invention may increase the quality of the image relative to the remaining area 930 of the display device 110. Thus, in various embodiments of the invention, the quality of the image produced across display device 110 may be increased in area 920 relative to remaining area 930.

When "modification" of an image presented on display device 110 is discussed herein, it shall be understood that what is intended is that a subsequent image displayed on display device 110, is different than a prior image displayed on display device 110. Thus, graphics processing device and display device 110, or other device(s) discussed herein, "modify" an image by causing a first image to be displayed and then a second image to be displayed which is different than the first image. Any other change of an image discussed herein, for example, increasing or decreasing of image quality, shall also be understood to mean that a subsequent image is different than a prior image. Note that a change or modification of an image may include changing or modifying only a portion of the image. Thus, some portions of a prior image may be the same as a subsequent image, while other portions may be different. In other situations, the entirety of a prior image may be different than a subsequent image. It shall be understood that the modification of an area or an entirety of an image does not necessarily mean every finite portion of the area or entirety are changed (for example, each pixel), but rather that the area or entirety may be changed in some potentially consistent, predefined, or ordered manner (for example, the quality of the image is changed).

Increasing the quality of the image may include increasing the quality of any one or more of the below non-exclusive list of graphical characteristics, in addition to other possible characteristics known in the art:

Resolution: The number of distinct pixels that may be displayed in one or more dimensions. For example, "1024×768" means 1024 pixels displayed in height and 768 pixels displayed in width.

Shading: Variation of the color and brightness of graphical objects dependent on the artificial lighting projected by light sources emulated by graphics processing device 130.

Texture-mapping: The mapping of graphical images or "textures" onto graphical objects to provide the objects with a particular look. The resolution of the textures influence the quality of the graphical object to which they are applied.

Bump-mapping: Simulation of small-scale bumps and rough gradients on surfaces of graphical objects.

Fogging/participating medium: The dimming of light when passing through non-clear atmosphere or air.

Shadows: Emulation of obstruction of light.

Soft shadows: Variance in shadowing and darkness caused by partially obscured light sources.

Reflection: Representations of mirror-like or high gloss reflective surfaces.

Transparency/opacity (optical or graphic): Sharp transmission of light through solid objects.

Translucency: Highly scattered transmission of light through solid objects.

Refraction: Bending of light associated with transparency.

Diffraction: Bending, spreading and interference of light passing by an object or aperture that disrupts the light ray.

Indirect illumination: Surfaces illuminated by light reflected off other surfaces, rather than directly from a light source (also known as global illumination).

Caustics (a form of indirect illumination): Reflection of light off a shiny object, or focusing of light through a transparent object, to produce bright highlights on another object.

Anti-aliasing: The process of blending the edge of a displayed object to reduce the appearance of sharpness or jagged lines. Typically an algorithm is used that samples colors around the edge of the displayed object in to blend the edge to its surroundings.

Frame rate: For an animated image, the number of individual frames presented during a certain period of time to render movement within the image.

3D: Visual and temporal characteristics of an image which cause the image to appear to be three dimensional to a viewer.

Figure 10A:
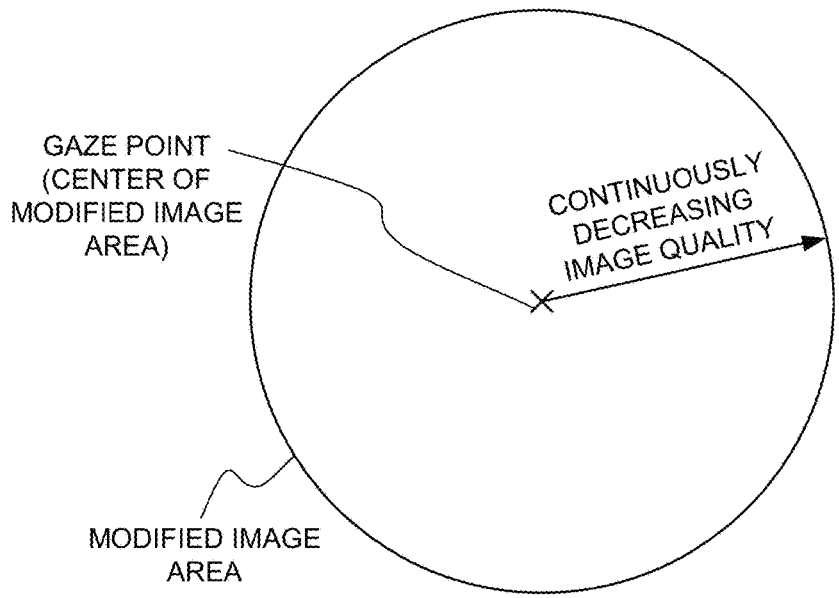
FIG. 10A is a diagram of how image quality may continuously vary within a modified image area.
Figure 10B:
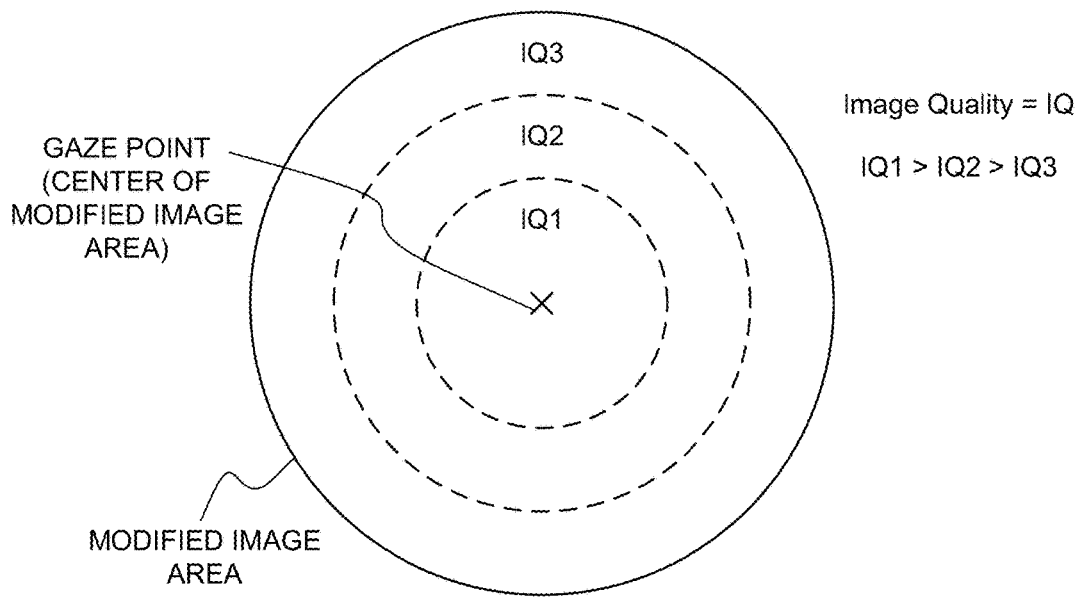
FIG. 10B is a diagram of how image quality may vary in steps within a modified image area.

The size and shape of the area of the image which may be modified to appear in greater quality can vary depending on the embodiment. Merely by way of example, the shape of the area may be circular, oval, square, rectangular, or polygonal. In some embodiments, the quality of the image within the area may be uniformly increased. In other embodiments, the increase in quality of the image may be greatest at the center of the area (i.e., proximate to the gaze point), and decrease towards the edges of the area (i.e., distal to the gaze point), perhaps to match the quality of the image surrounding the area. To demonstrate, FIG. 10A shows how image quality may decrease in a linear or non-liner continuous manner from the center of a gaze area outward, while FIG. 10B shows how image quality may decrease in a stepped manner from the center of a gaze area outward.

In some embodiments, modifying the image displayed on display device 110 may occur in response to the detection of a change in the gaze point. This may occur in a number of fashions, some of which are described below.

In some embodiments, an entirety of the image may be modified during the period of change in the gaze point of the user, and once the change in the gaze point of the user ceases, either the area around end gaze point of the user or a remainder of the image (portions of the image not around the end gaze point) may be modified. Merely by way of example, in one embodiment, the quality of the entire image may be increased during movement of the user's gaze (sometimes referred to as a saccade), but the increase in quality may only be sustained in an area around the user's end gaze point once the saccade is complete (i.e., the quality of the remainder of the image may be decreased upon completion of the saccade). In a different embodiment, the quality of the entire image may be decreased during a saccade, but the decrease in quality may only be sustained areas besides around the user's end gaze point once the saccade is complete (i.e., the quality of the area of the image around the user's end gaze point may be increased upon completion of the saccade).

Additionally, the use of other system resources, including for example, processor/computer and related resources, may also be modified during a user's saccade. For example, non-graphical operations may be supplemented by the resources of processor/computer and graphics processing device, during a saccade. More specifically, during a saccade, non-graphical calculations necessary for other system operations may proceed at greater speed or efficiency because additional resources associated with processor/computer and graphics processing device are made available for such operations.

In some embodiments, modifying the image displayed on display device 110 may include modifying a portion of the image in an area around an anticipated gaze point of the user, potentially by increasing the quality thereof. The anticipated gaze point may be determined based on the change in the gaze point of the user. To determine the anticipated gaze point of a user, eye tracking device and/or another processor (i.e, the computer or game consoler's processor), may determine a rate of the change in the gaze point of the user on display device, and determine the anticipated gaze point based at least in part on this rate of the change.

The rate of change of the gaze point of the user, also referred to as the velocity or speed of a saccade by the user is directly dependent on the total change in the gaze point of the user (often referred to as the amplitude of the saccade). Thus, as the intended amplitude of a user's saccade increases, so does the speed of the saccade. While the saccade of a human user can be as fast as 900°/second in humans, for saccades of less than or about 60°, the velocity of a saccade is generally linearly and directly dependent on the amplitude of the saccade. For example, a 10° amplitude is associated with a velocity of 300°/second and a 30° amplitude is associated with a velocity of 500°/second. For saccades of greater than 60°, the peak velocity starts to plateau toward the maximum velocity attainable by the eye (900°/second). In response to an unexpected stimulus, a saccade normally takes about 200 milliseconds (ms) to be initiated and then lasts from about 20 to about 200 ms. Based on these relationships between saccade speed and amplitude, embodiments of the invention may determine anticipated gaze points based on saccade velocity. Other predetermined models of mathematical relationships between saccade speed and amplitude may also be employed by various embodiments of the invention to determine an anticipated gaze point.

In some embodiments, the portion of the image modified around the anticipated gaze point may also include the portion of the image around the original gaze point (i.e., the gaze point from which the user's saccade started). While the shape of the portion of the image modified may be any of those shapes described above, in some embodiments it may be a triangle or a trapezoidal shape having a progressively greater width perpendicular to a direction of the saccade as shown in FIG. 11.

Figure 11:
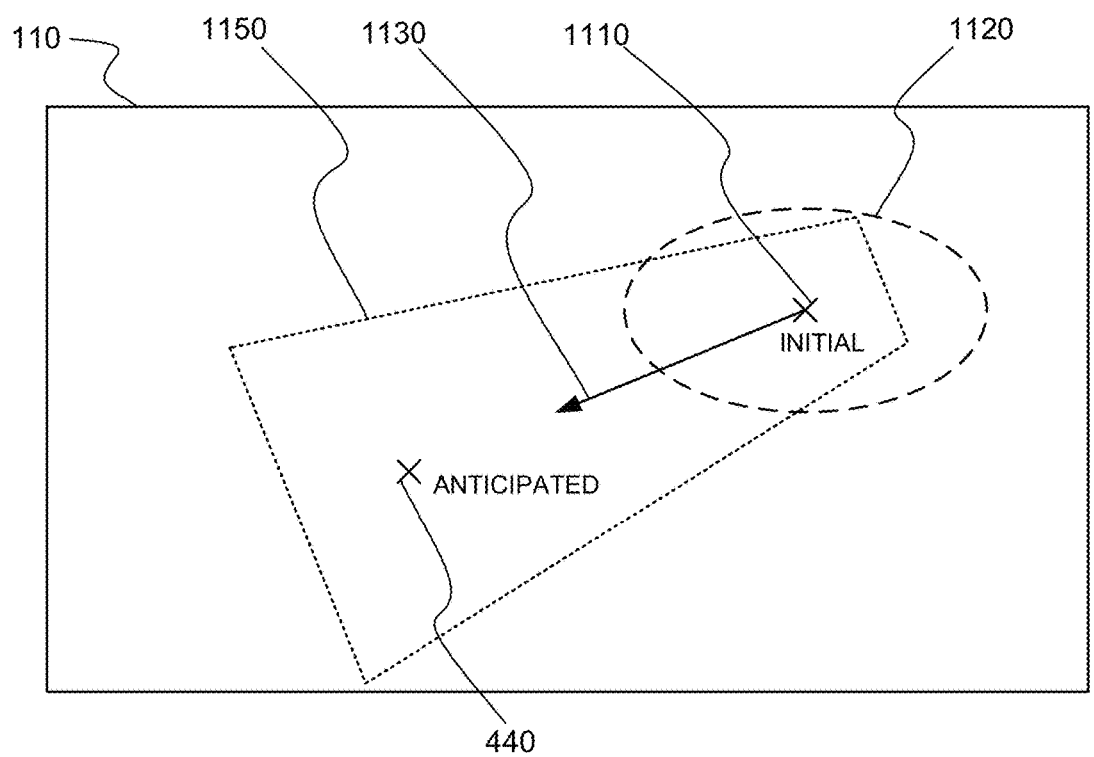
FIG. 11 is a view of a display device of the invention in which image modification is occurring in response to a detected change in a user's gaze point.

In FIG. 11, display device 110 is shown, and an initial user gaze point 1110 is shown thereon. Prior to any change in initial gaze point 1110, embodiments of the invention may provide increased graphics quality in area 1120. When a user saccade, represented by arrow 1130, is detected by eye tracking device, the size and shape of area 1120 may change to accommodate both initial gaze point 1110 and anticipated gaze point 1140. The changed area 1150, while being triangular and/or trapezoidal in this embodiment, may be shaped and sized differently in other embodiments. Merely by way of example, an entire side of display device 110 from the initial gaze point to the edges of the display in the direction of the saccade may also be included in changed area 1150 to account for more possibilities of where the user's gaze point may end. In other embodiments, a circular, oval, or square changed area 1150 may be provided. In yet other embodiments, changed area 1150 may include separate and distinct areas around the initial gaze point 1110 and anticipated gaze point 1140.

In some embodiments, the size or shape of the area around the gaze point for which an image is modified (or which remains unmodified from a heightened quality in various embodiments), is dynamic. This may occur based at least in part on any number of factors, including the current location of the gaze point relative to the image or display device. Merely by way of example, if a user moves their gaze point to a certain portion of the screen, a predefined portion of the screen may be modified via increased quality therein (for example, a corner portion of the display having a map of a virtual area in a video game). In some embodiments, if enough user saccades having one or more predefined characteristics are detected in predefined amount of time, the entirety of the display may be modified to be rendered in greater quality.

In another embodiment of the invention, a non-transitory computer readable medium having instructions thereon for presenting graphics on display device 110 is provided. The instructions may be executable by one or more processors to at least display an image on display device 110. The instructions may also be executable to receive information from eye tracking device indicative of at least one of a gaze point of a user on display device 110, or a change in the gaze point of the user on display device 110. The instructions may further be executable to cause graphics processing device to modify the image displayed on display device 110 based at least in part on the gaze point of the user on display device 110, or the change in the gaze point of the user on display device 110. Thus, a non-transitory computer readable medium able to implement any of the features described herein in relation to other embodiments is also provided.

Figure 12:
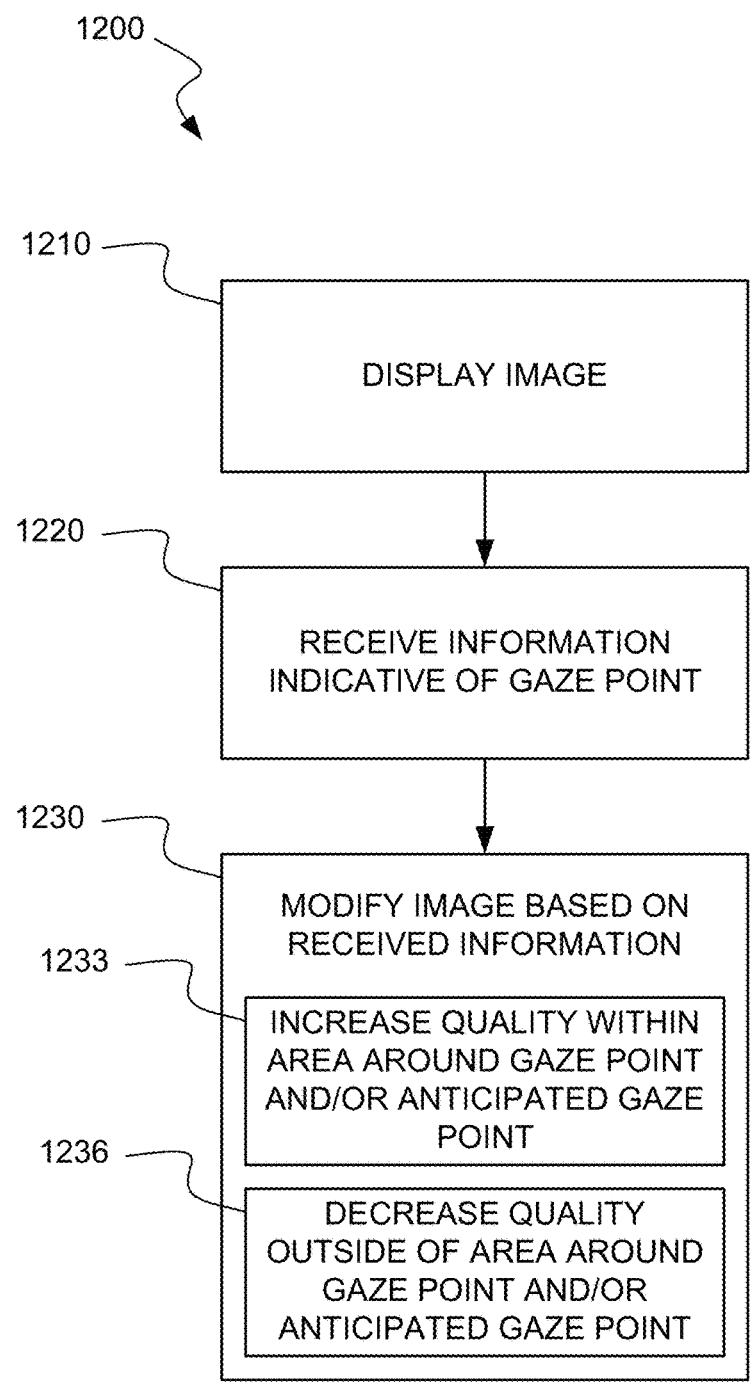
FIG. 12 is flow diagram of one possible method of the invention for modifying an image based on a user's gaze point.

In another embodiment of the invention, a method 1200 for presenting graphics on display device 110 is provided as shown in FIG. 12. At step 1210, method 1200 may include displaying an image on display device 110. At step 1220, method 1200 may also include receiving information from eye tracking device indicative of at least one of a gaze point of a user on display device 110, or a change in the gaze point of the user on display device 110. At step 1230, method 1200 may further include causing graphics processing device to modify the image displayed on display device 110 based at least in part on the gaze point of the user on display device 110, or the change in the gaze point of the user on display device 110. Step 1230 may include, at step 1233, increasing the quality of the image in an area around the gaze point of the user, relative to outside the area. Step 1230 may also include, at step 1236, decreasing the quality of the image outside an area around the gaze point of the user, relative to inside the area. Thus, a method to implement any of the features described herein in relation to other embodiments is also provided.

In some embodiments, the systems and methods described herein may be toggled on and off by a user, possibly to account for multiple additional viewers of display device 110 being present. In other embodiments, the systems and methods described herein may automatically toggle on when only one user is viewing display device 110 (as detected by eye tracking device), and off when more than one user is viewing display device 110 (as detected by eye tracking device). Additionally, in some embodiments, the systems and methods described herein may allow for reduction in rendering quality of an entire display device 110 when no viewers are detected, thereby saving system resources and power consumption when display device 110 is not the primary focus of any viewer.

In other embodiments, the systems and methods described herein may allow for modifying multiple portions of an image on display device 110 to account for multiple viewers as detected by eye tracking device. For example, if two different users are focused on different portions of display device 110, the two different areas of the image focused on may be rendered in higher quality to provide enhanced viewing for each viewer.

In yet other embodiments, data associated with an image may inform the systems and methods described herein to allow prediction of which areas of an image may likely be focused on next by the user. This data may supplement data provided by eye tracking device to allow for quicker and more fluid adjustment of the quality of the image in areas likely to be focused on by a user. For example, during viewing of a sporting event, a picture-in-picture of an interview with a coach or player may be presented in a corner of the image. Metadata associated with the image feed may inform the systems and methods described herein of the likely importance, and hence viewer interest and likely focus, in the sub-portion of the image.

Trajectory Adjustment of Projectiles in Virtual Reality

In virtual reality embodiments, when virtual objects are thrown or otherwise launched by user action, a problem exists whereby the user cannot easily estimate the weight of the object and thus how far the object, now a projectile, will fly when launched. Given that accurate distances may be necessary to make the virtual interaction usable or successful, gaze detection may serve the purpose of assisting in increasing in accurate placement of the desired target location for the projectile.

In some embodiments, eye tracking devices may be used to determine the gaze direction of a user launching a virtual object, and allow for the location of the gaze direction on a virtual display to either be used to determine, or assist in determining, the intended destination of the projectile. In some embodiments, the exact gaze location on the virtual display may be used as the intended target of the user.

In other embodiments, the gaze location on the virtual display may merely inform the software process of the intended target, and this may affect, to a variable degree depending on the algorithm, the calculated target for a projectile. Thus, while an initial target may be calculated by the algorithm, and depend on factors such as speed of the throwing or other motion which initiated the launch of the projectile and the virtually assigned weight of the object, the gaze direction may be used, to variable degrees, as assigned by the algorithm, to modify the calculated initial target.

Distributed Multi-Camera Array on/in VR Lens

Figure 7A:
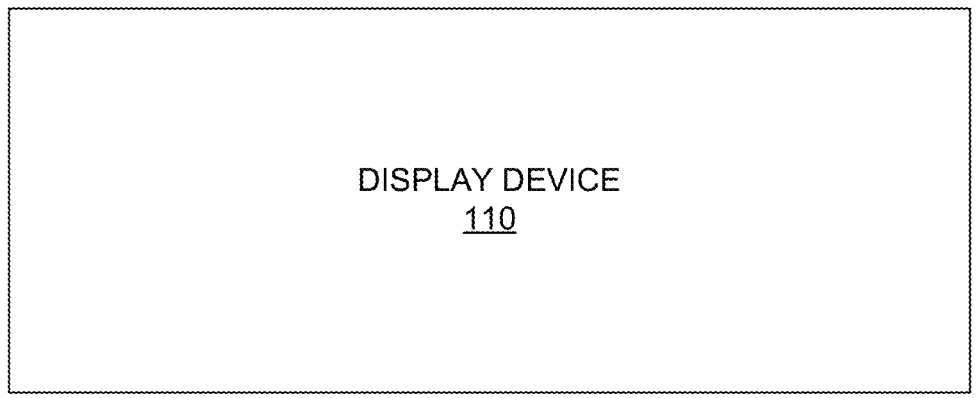
FIG. 7A shows one system embodiment of the invention for sensor/illuminator arrays disposed on and/or in a lens of a wearable device.
Figure 7A:
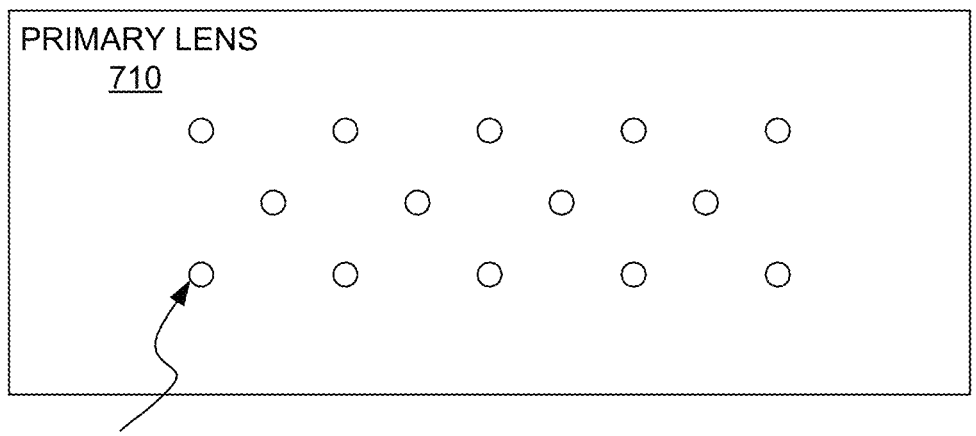

In traditional virtual reality or other wearable devices, it can be challenging to position image sensors and camera associated with an eye tracking device so that they can obtain good imaging, but without interfering with the viewing lens of the display system therein. In order to solve this problem, one solution provided by various embodiments of the invention is to dispose one or more arrays of miniature cameras/image/light sensors (as well as illuminators as discussed herein) on or in the lenses directly in front of the user's eyes. Because the cameras are very small (e.g., 1 $mm^3$) and very close to the user's eyes, they will essentially appear to be invisible to the user, as they are not within active focal distance of the user. As shown in FIG. 7A, in front of a display device 110 of a given system, a viewing/primary lens 710 may be present, and an array of cameras/illuminators 720 may also be present on or in lens 710. Cameras/illuminators 720 are shown larger than to-scale for the purposes of demonstration in this figure. FIG. 7A will be discussed below in further detail.

While each camera of an array may only have limited resolution, when the images of all cameras are combined and reconstructed by an associated processing device, standard images may be obtained. Additionally, because an array is used, additional depth information of the image may be obtained over the use of a single camera or image sensor observing the eye(s).

User and Obstruction Presence Verification for Safe Light Source Operation

Consumer device must meet various standards of safety with respect to light and laser sources near a user's eyes. The closer the user is to the consumer device light/laser source, the lower the magnitude of illumination allowed to satisfy the various standards.

In some embodiments, devices herein may include safety mechanism arranged to protect the user and verify that the standards are met. In one embodiment, the eye tracking devices herein may determine if a user is present in front of the device via image sensors, and react accordingly.

If no user is present, illumination levels of the display and/or eye tracking illuminators are lowered to be safe at any distance. Because no user is present, the display and/or illuminators will be illuminated at a safe level for any condition that arises. However, if a user is determined to be present, the distance from any display and/or eye tracking subsystems such as illuminators may be calculated, and the maximum allowable illumination thereof allowed by the system may be restored. In some embodiments, if an eye tracking device determines no user is present, a display device may be turned off in order to save power.

In some embodiments, the systems herein may also be able to determine if any illuminator is obstructed, either by direct detection of the obstruction by an image sensor, or by lack of detection by an image sensor of light from a particular illuminator. If an illuminator or other light emitting device such as a display is determined to be obstructed, such light producing devices may be dimmed or deactivated entirely, in order to save power.

Visibility Reduction of Illumination Devices and Image Sensors in VR Devices

In some embodiments, in order to arrange illumination devices and image sensors of the invention in the most advantageous position, flexible printed circuit (FPC) supported illuminators and image sensors may be sunk into the lenses of virtual reality or other display devices, perhaps in locations as shown in FIG. 7A. LEDs or other illuminators, as well as image sensors, may be located on very thin FPCs, and then orientated so as to minimize the visible profile thereof.

Merely by way of example, illuminators and image sensors may be mounted on FPCs such that the illuminator or image sensor is mounted facing the user, but only the profile of the FPC (i.e., the thickness of the FPC) is viewed directly by a user of the device. In some embodiments, the FPC may be attached to the illuminator or image sensor such it couples to more than one side of the illuminator/sensor. In this manner, capture of light to or directed from the illuminator/sensor may be improved.

Figure 7B:
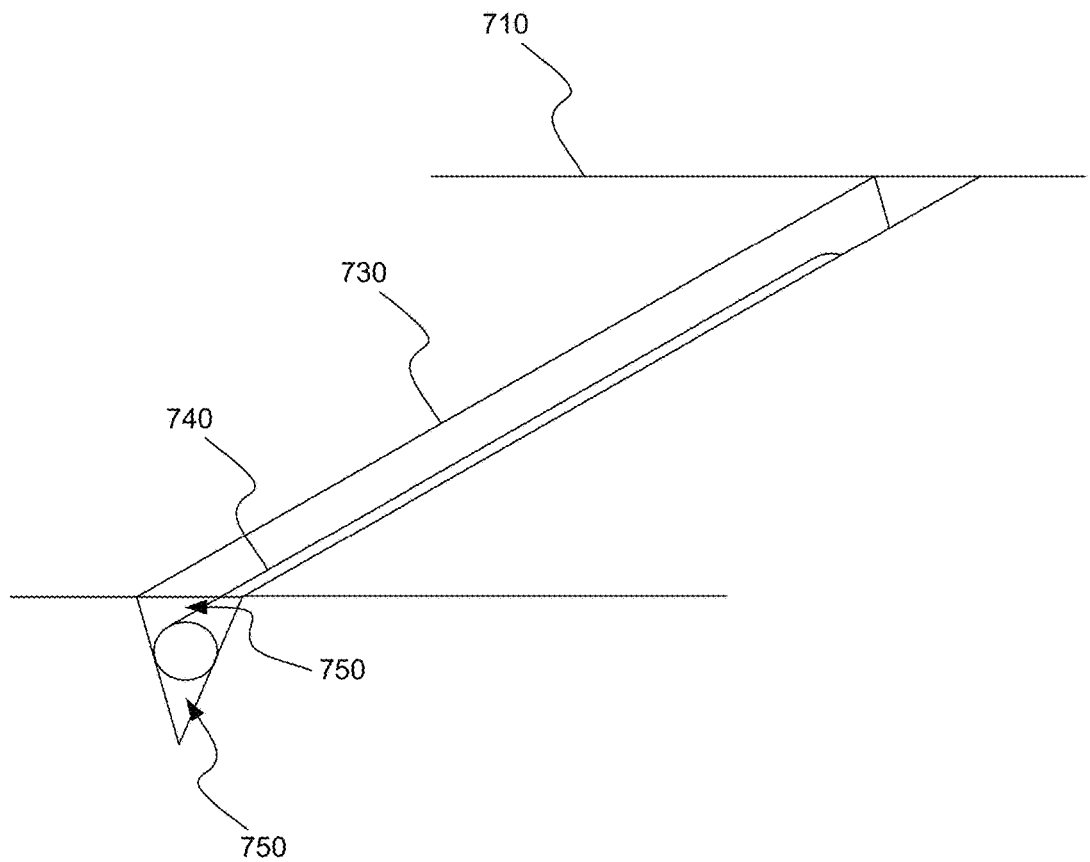
FIG. 7B shows a close-up view of one embodiment of the invention where optical fibers are disposed within grooves on a primary viewing lens.

In these and other embodiments, another method may also be used to minimize the appearance of illuminators in a virtual reality or other display device. In these embodiments, optical fibers may be embedded into grooves on the front (user) side of the viewing lens of the device. FIG. 7B shows such a groove 730 and the optical fiber 740 deposited in the surface of lens 710. The optical fibers may be numerously distributed across the front side of the lens so as to generate the illumination necessary for eye tracking. LEDs or other illumination sources such as luminescent diodes may be coupled to the end of the optical fibers at the edge, or away from, the lens.

Any void in the grooves where the optic fibers are placed may be filled with a substance 750 such as glue or other adhesive to maintain the position of the fiber, and to minimize refraction therein. The substance may have the same, or similar, refraction index to the lens itself in order to minimize visible distortion of the lens to the user.

Figure 7C:
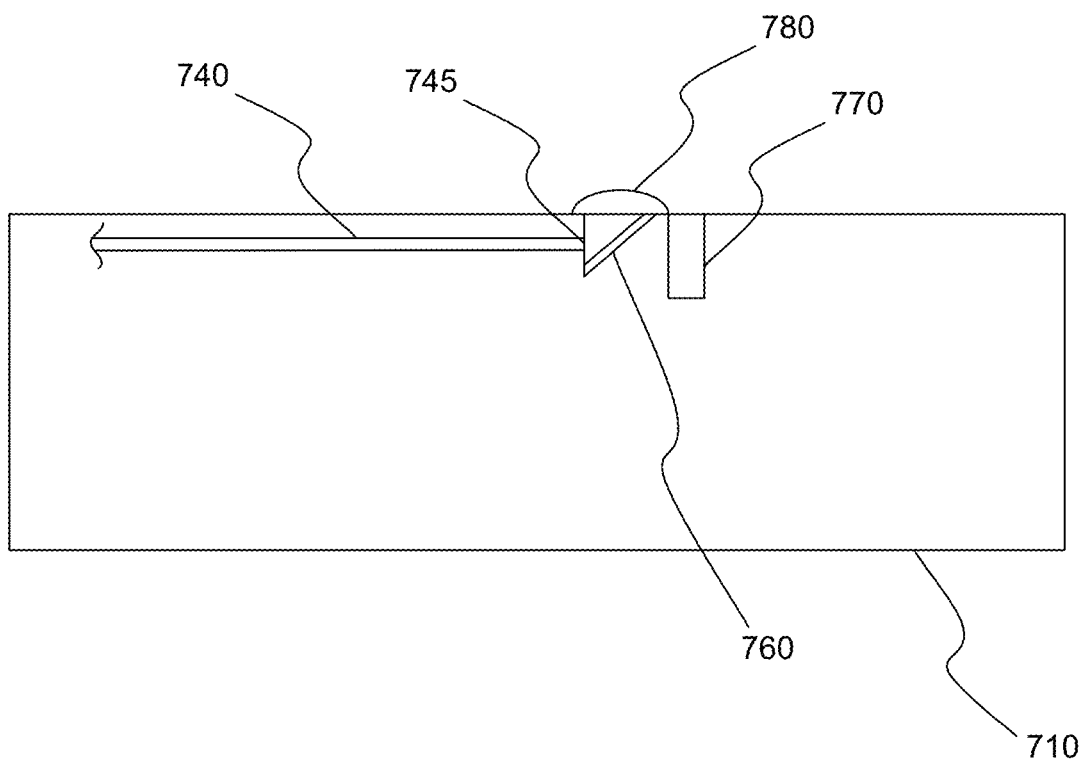
FIG. 7C shows a profile view of a termination point of the optical fiber of FIG. 7B.

As shown in FIG. 7C, an angled and/or reflected surface 760 within the lens 710 at the termination point 745 of the optical fiber 740 may guide light from the end of the optical fiber toward the eye. To further minimize potentially stray light from the optical fiber within the lens, a light absorptive material 770 may also be disposed near the termination point of the optical fiber, perhaps behind the angled surface. A beam shaping material 780 such as epoxy, silicone, or similar substance may also be applied to the lens near the termination point to assist in directing light toward the proper location on the user's eye.

Exemplary Computer System

Figure 8:
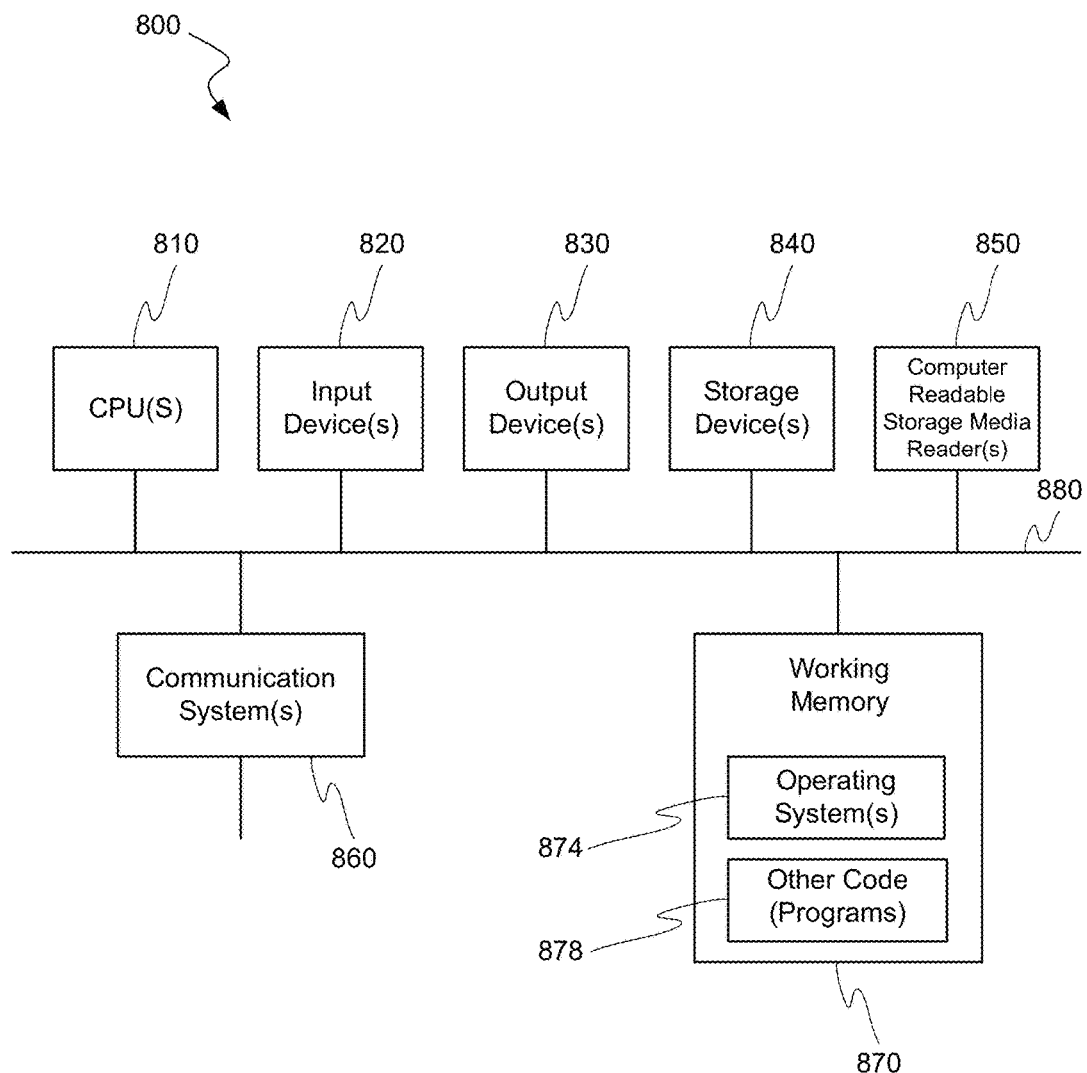
FIG. 8 is a block diagram of an exemplary computer system capable of being used in at least some portion of the apparatuses or systems of the present invention, or implementing at least some portion of the methods of the present invention.

The above is a block diagram illustrating an exemplary computer system 800, as shown in FIG. 8, in which any of the embodiments of the present invention may be implemented. This example illustrates a computer system 800 such as may be used, in whole, in part, or with various modifications, to provide the functions of the systems and methods described above.

The computer system 800 is shown including hardware elements that may be electrically coupled via a bus 890. The hardware elements may include one or more central processing units 810, one or more input devices 820 (e.g., eye-tracking device, whether integrated or not with another device; a mouse; a keyboard; a touchpad; a microphone; handheld controller; etc.), and one or more output devices 830 (e.g., a display device, a wearable device having a display, a printer, etc.). The computer system 800 may also include one or more storage device 840. By way of example, storage device(s) 840 may be transitory and/or non-transitory disk drives, optical storage devices, solid-state storage device such as a random access memory ("RAM") and/or a read-only memory ("ROM"), which can be programmable, flash-updateable and/or the like.

The computer system 800 may additionally include a computer-readable storage media reader 850, a communications system 860 (e.g., a modem, a network card (wireless or wired), an infra-red communication device, Bluetooth™ device, cellular communication device, etc.), and working memory 880, which may include RAM and ROM devices as described above. In some embodiments, the computer system 800 may also include a processing acceleration unit 870, which can include a digital signal processor, a special-purpose processor and/or the like.

The computer-readable storage media reader 850 can further be connected to a computer-readable storage medium, together (and, optionally, in combination with storage device(s) 840) comprehensively representing remote, local, fixed, and/or removable storage devices plus storage media for temporarily and/or more permanently containing computer-readable information. The communications system 860 may permit data to be exchanged with a network, system, computer and/or other component described above.

The computer system 800 may also include software elements, shown as being currently located within a working memory 880, including an operating system 884 and/or other code 878. It should be appreciated that alternate embodiments of a computer system 800 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 800 may include code 878 for implementing any or all of the function of the various elements of the architecture as described herein. For example, software, stored on and/or executed by a computer system such as system 800, can provide the functions of the methods and systems discussed above. Methods implementable by software on some of these components have been discussed above in more detail.

The invention has now been described in detail for the purposes of clarity and understanding. However, it will be appreciated that certain changes and modifications may be practiced within the scope of the appended claims.

What is claimed is:

1. A system for determining a gaze direction of a user in a wearable device, wherein the system comprises:
    a display device;
    a primary lens disposed in front of the display device;
    an illuminator configured to illuminate an eye of a user, wherein the illuminator is disposed in the primary lens, and wherein the illuminator comprises a plurality of optical fibers; wherein the optical fibers are deposited in grooves in a surface of the lens and are numerously distributed across a front side of the lens; wherein any void in the grooves where the optical fibers are placed are filled with a substance to maintain a position of the optical fibers, and to minimize refraction therein; and wherein the substance has a same, or similar, refraction index to the lens itself in order to minimize visible distortion of the lens to the user; and an imaging device disposed in the primary lens to detect light reflected by the eye of the user.

2. The system for determining a gaze direction of a user in a wearable device of claim 1, wherein:
    the imaging device is no larger than about 1 millimeter by about 1 millimeter by about 1 millimeter.

3. The system for determining a gaze direction of a user in a wearable device of claim 1, wherein:
    the imaging device is disposed within a cavity in the primary lens.

4. The system for determining a gaze direction of a user in a wearable device of claim 3, wherein:
    an additional substance having a substantially similar refraction index to the primary lens is disposed within the cavity so as to smooth a surface of the primary lens.

5. The system for determining a gaze direction of a user in a wearable device of claim 1, wherein the additional substance comprises:
    a flow-able hardening substance.

6. The system for determining a gaze direction of a user in a wearable device of claim 1, wherein:
    the imaging device comprises a sensor disposed on a flexible printed circuit; and
    a width and a length of the flexible printed circuit is orientated orthogonally to a viewing surface of the primary lens.

7. The system for determining a gaze direction of a user in a wearable device of claim 1, wherein:
    the illuminator is no larger than about 1 millimeter by about 1 millimeter by about 1 millimeter.

8. The system for determining a gaze direction of a user in a wearable device of claim 1, wherein:
    the illuminator is disposed within a cavity in the primary lens.

9. The system for determining a gaze direction of a user in a wearable device of claim 8, wherein:
    an additional substance having a substantially similar refraction index to the primary lens is disposed within the cavity so as to smooth a surface of the primary lens.

10. The system for determining a gaze direction of a user in a wearable device of claim 9, wherein the additional substance comprises:
    a flow-able hardening substance.

11. The system for determining a gaze direction of a user in a wearable device of claim 1, wherein the system further comprises:
    a reflector disposed in the cavity to reflect light from the optical fiber toward the user.

12. The system for determining a gaze direction of a user in a wearable device of claim 1, wherein the system further comprises:
    a secondary lens at the surface of the primary lens to refract light from the optical fiber toward the user.

13. The system for determining a gaze direction of a user in a wearable device of claim 12, wherein the secondary lens comprises:
a flow-able hardening substance.

14. The system for determining a gaze direction of a user in a wearable device of claim 1, wherein:
the primary lens is configured to guide light from the illuminator toward the eye of the user.

15. The system for determining a gaze direction of a user in a wearable device of claim 1, wherein:
the primary lens comprises a light guide configured to guide light from the illuminator toward the eye of the user.

16. The system for determining a gaze direction of a user in a wearable device of claim 1, wherein:
the primary lens is configured to focus light toward the imaging device.

17. The system for determining a gaze direction of a user in a wearable device of claim 1, wherein the primary lens comprises:
a Fresnel lens.

18. The system for determining a gaze direction of a user in a wearable device of claim 1, further comprising a plurality of illumination sources, wherein the illumination sources are coupled to the end of the optical fibers at the edge, or away from, the lens.

19. A system for determining a gaze direction of a user in a wearable device, wherein the system comprises:
a display device;
a primary lens disposed in front of the display device;
an illuminator disposed on or in the primary lens configured to illuminate an eye of a user, wherein the illuminator comprises a plurality of optical fibers; wherein the optical fibers are deposited in grooves in a surface of the lens and are numerously distributed across a front side of the lens; wherein any void in the grooves where the optical fibers are placed are filled with a substance to maintain a position of the optical fibers, and to minimize refraction therein; and wherein the substance has a same, or similar, refraction index to the lens itself in order to minimize visible distortion of the lens to the user; and an imaging device disposed on or in the primary lens to detect light reflected by the eye of the user.

20. The system for determining a gaze direction of a user in a wearable device of claim 19, wherein:
the imaging device is disposed within a cavity in the primary lens.

21. The system for determining a gaze direction of a user in a wearable device of claim 19, wherein:
the primary lens is configured to guide light from the illuminator toward the eye of the user.

22. The system for determining a gaze direction of a user in a wearable device of claim 19, wherein:
the primary lens comprises a light guide configured to guide light from the illuminator toward the eye of the user.

23. A system for determining a gaze direction of a user in a wearable device, wherein the system comprises:
a display device;
a primary lens disposed in front of the display device;
an illuminator disposed on or in the primary lens configured to illuminate an eye of a user, wherein the illuminator comprises a plurality of optical fibers; wherein the optical fibers are deposited in grooves in a surface of the lens and are numerously distributed across a front side of the lens; wherein any void in the grooves where the optical fibers are placed are filled with a substance to maintain a position of the optical fibers, and to minimize refraction therein; and wherein the substance has a same, or similar, refraction index to the lens itself in order to minimize visible distortion of the lens to the user; and an imaging device.

24. The system for determining a gaze direction of a user in a wearable device of claim 23, wherein the imaging device comprises a profile sensor.

25. The system for determining a gaze direction of a user in a wearable device of claim 23, wherein:
the primary lens is configured to guide light from the illuminator toward the eye of the user.

26. The system for determining a gaze direction of a user in a wearable device of claim 23, wherein:
the primary lens comprises a light guide configured to guide light from the illuminator toward the eye of the user.

27. The system for determining a gaze direction of a user in a wearable device of claim 23, wherein:
the primary lens is configured to focus light toward the imaging device.

28. The system for determining a gaze direction of a user in a wearable device of claim 23, wherein the primary lens comprises:
a Fresnel lens.

* * * * *